United States Patent
Hur et al.

(10) Patent No.: US 9,469,603 B2
(45) Date of Patent: *Oct. 18, 2016

(54) REACTION PRODUCT OF HYDRAZINE DERIVATIVES AND CARBON DIOXIDE

(71) Applicant: SOGANG UNIVERSITY RESEARCH FOUNDATION, Seoul (KR)

(72) Inventors: Nam Hwi Hur, Seoul (KR); Byeong No Lee, Yongin-si (KR)

(73) Assignee: Sogang University Research Foundation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/484,449

(22) Filed: Sep. 12, 2014

(65) Prior Publication Data

US 2015/0094490 A1    Apr. 2, 2015

Related U.S. Application Data

(63) Continuation of application No. PCT/KR2012/001817, filed on Mar. 13, 2012.

(30) Foreign Application Priority Data

Mar. 12, 2012  (KR) ................. 10-2012-0025061

(51) Int. Cl.
| | | |
|---|---|---|
| *C07C 261/00* | (2006.01) | |
| *C07C 271/02* | (2006.01) | |
| *C07D 213/77* | (2006.01) | |
| *C07C 281/02* | (2006.01) | |
| *C07C 251/80* | (2006.01) | |
| *C07C 251/86* | (2006.01) | |

(52) U.S. Cl.
CPC ........... *C07C 271/02* (2013.01); *C07C 251/80* (2013.01); *C07C 251/86* (2013.01); *C07C 281/02* (2013.01); *C07D 213/77* (2013.01)

(58) Field of Classification Search
CPC . C07C 251/80; C07C 251/86; C07C 271/02; C07C 281/02; C07C 213/77; C07D 213/77
See application file for complete search history.

(56) References Cited

U.S. PATENT DOCUMENTS

| | | |
|---|---|---|
| 2,878,103 A | 3/1959 | Robell et al. |
| 3,551,226 A | 12/1970 | Allan |
| 3,598,546 A | 8/1971 | Good |
| 4,804,442 A | 2/1989 | Rigsby |
| 6,849,161 B2 | 2/2005 | Richard |

FOREIGN PATENT DOCUMENTS

| | | |
|---|---|---|
| JP | 08-134038 | 5/1996 |
| JP | 08 134038 | * 5/1998 |
| JP | 11-349554 | * 12/1999 |

OTHER PUBLICATIONS

Byeongno et al. (Isolation and Structural Characterization of the Elusive 1:1 adduct of hydrazine and carbon dioxide, Chem Comm, 47 11219-11221, published on the web Sep. 15, 2011).*
JP08-134038, 1998, machine translation.*
JP11-134038 "JP11" (1999, all references to JP11 are to a machine translation submitted with IDS).*
Caplow, (Kinetics of Carbamate Formation and Breakdown, Journal of the American Chemical Society, 90 (24), 1968).*
Nachbaur et al. (A Simple and Harmless Prepa1•ation of Anhydrous Hydrazine, Monatsbefte für Chemie 102, 1718-1723, 1971).*
MadSci Network 2001.*
Int'l. Search report of PCT/KR2012/001817 dated Feb. 18, 2013.
Byeongno Lee et al., "Isolation and structural characterization of the elusive 1 : 1 adduct of hydrazine and carbon dioxide", Chem. Commun., 2011, vol. 47, pp. 11219-11221.
Byeongno Lee et al., "Synthesis of Azines in Solid State: Reactivity of Solid Hydrazine with Aldehydes and Ketones", Organic Letters 2011, vol. 13, No. 24, pp. 6386-6389.

* cited by examiner

*Primary Examiner* — Yevegeny Valenrod
*Assistant Examiner* — Blaine G Doletski
(74) *Attorney, Agent, or Firm* — Greer, Burns & Crain, Ltd.

(57) ABSTRACT

The present invention relates to the synthesis of a novel compound, in which liquid hydrazine and the derivatives thereof react with excess carbon dioxide to enable the carbon dioxide to chemically bond to the hydrazine and the derivatives thereof. To this end, high-pressure carbon dioxide is used to synthesize hydrazine and the derivatives thereof to which the carbon dioxide is bonded in a pure form with no water and no by-product. Furthermore, the present invention provides a method for utilizing the above-described compounds by reacting the compounds with carbonyl compounds.

20 Claims, 22 Drawing Sheets

REACTION PRODUCT OF HYDRAZINE DERIVATIVES AND CARBON DIOXIDE

CROSS-REFERENCE TO RELATED APPLICATION

This application is a continuation of International Patent Application No. PCT/KR2012/001817 filed on Mar. 13, 2012, claiming priority based on Korean Patent Application No. 10-2012-0025061 filed on Mar. 12, 2012, the contents of all of which are incorporated herein by reference in their entirety.

TECHNICAL FIELD

The embodiments described herein pertain generally to preparing a new compound, in which carbon dioxide is chemically bonded to a hydrazine derivative through reaction of hydrazine and derivatives thereof with carbon dioxide, and to applying the compound.

The embodiments described herein pertain generally to preparing a new compound, in which carbon dioxide is chemically bonded to a hydrazine derivative by being reacted liquid hydrazine and derivatives thereof with excess carbon dioxide.

To achieve this, the hydrazine and derivatives thereof in which carbon dioxide is chemically bonded to a hydrazine derivative is synthesized. The embodiments described provide an application of the compound through a reaction of the compound with a carbonyl compound.

BACKGROUND

Hydrazine derivatives such as hydrazine, mono-methyl-hydrazine (MMH) and di-methyl-hydrazine (DMH) exist in a liquid state at a room temperature and at an atmospheric pressure, and are variously used in various fields such as blowing agents, precursors for agricultural pesticides and medicines, and rocket fuel. Since the hydrazine derivatives are toxic and highly reactive, it is difficult to transport or store them, thereby, resulting in difficulty in treating the same.

As means to reduce the above-described problems of the liquid hydrazine derivatives, it has been suggested to make solid hydrazinium salts and use them, instead of hydrazine. Meanwhile, U.S. Pat. Nos. 3,551,226 and 2,878,103 suggested partially reacting hydrazine derivatives with carbon dioxide which is a flame retardant gas to prepare and use a gel or azeotropic mixture. That is, from U.S. Pat. No. 2,878,103, it was known that when carbon dioxide is blown into and reacted with a hydrazine solution under the presence of a large amount (>46 wt %) of water, the reactant is present in a mixture form, which mostly consists of carbazic acid ($HCO_2N_2H_3$) and hydrazinium carbazate ($N_2H_5CO_2N_2H_3$), and in which a ratio of the hydrazine and the carbon dioxide is not constant. In addition, U.S. Pat. No. 3,551,226 suggested reacting substituted hydrazine derivatives with carbon dioxide to produce very sticky gel and using the gel as a propellant.

Meanwhile, since most hydrazine and hydrazine derivatives necessarily accompany generation of water in preparation processes and form an azeotrope with water, it is significantly difficult to prepare pure hydrazine and derivatives thereof, from which water is completely removed. Such hydrazine and derivatives thereof would be used in many cases in the state of containing water, but are not suitable for cases necessarily requiring anhydrous hydrazine containing no water, e.g., cases where hydrazine and derivatives thereof are used as rocket fuel, or reactions need to be conducted in an environment having no water. For this reason, many researchers have conducted researches to prepare anhydrous hydrazine and derivatives thereof by removing water from hydrazine and derivatives thereof as reported in U.S. Pat. Nos. 6,849,161; 4,804,442; and 3,598,546, and others. However, the U.S. patents relate to methods for distillation at a significantly lower pressure (vacuum condition) than an atmospheric pressure. Those methods are complicated purification processes requiring high costs for installation and management of a vacuum distillation device.

Meanwhile, anhydrous hydrazine and derivatives thereof may cause occurrence of fire or explosion due to leakage or vaporization, and environmental pollution due to rapid reaction with peripheral metal materials, and further, absorb water thereby deteriorating their properties unless they are completely sealed. A preparation of an anhydrous hydrazine and the derivatives thereof is difficult, and the difficulty in transporting and storing an anhydrous compound results in limits in applying them to fields other than rocket fuel. Thus, it is important to develop new hydrazine derivatives, which are stable and highly reactive and contain no water, in order to overcome the foregoing problems.

SUMMARY

In light of the above-described problems of the liquid hydrazine derivatives, example embodiments synthesize a new hydrazine derivative compound, which has no problem in storage and transportation and is safe and convenient for use, and from which water is completely removed, to compensate the drawbacks of the existing liquid hydrazine derivatives and expand the fields, to which the hydrazine derivatives can be applied. That is, example embodiments provide a method for synthesizing a new hydrazine derivative compound, to which carbon dioxide is chemically bonded through reaction of carbon dioxide as a major green-house gas with liquid hydrazine derivatives, and for applying the new hydrazine derivative compound.

Example embodiments have synthesized a new compound, in which carbon dioxide is chemically bonded to hydrazine and derivatives thereof by reacting liquid hydrazine and derivatives thereof with excess carbon dioxide as having never been suggested, which is not the mixture in which hydrazine and derivatives thereof are partially reacted with each other. To this end, example embodiments have synthesized and analyzed hydrazine and derivatives thereof having no water and no by-products, to which pure carbon dioxide is bonded, by using carbon dioxide at a high pressure, and identified that the synthesis of the compounds, for which the analysis has been completed, can also be accomplished even in a milder synthesis condition.

A purpose of the present disclosure is provided a hydrazinium carboxylate derivative represented by the following Structural Formula II, which is synthesized by reacting a compound represented by the following Structural Formula I and carbon dioxide:

[Structural Formula I]

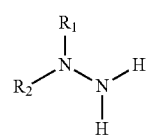

-continued

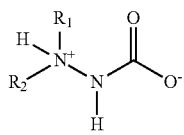

[Structural Formula II]

in Structural Formulas I and II, each of $R_1$ and $R_2$ is independently hydrogen; or, one of an aliphatic hydrocarbon group of 1 to 30 carbons, a substituted aliphatic hydrocarbon group of 1 to 30 carbons, a substituted aliphatic carbocyclic group of 1 to 30 carbons, a substituted aliphatic heterocyclic group of 1 to 30 carbons, a substituted aromatic cyclic group of 1 to 30 carbons, and a substituted aromatic heterocyclic group of 1 to 30 carbons; or, one of an aliphatic hydrocarbon group including at least one of Si, O, S, Se, N, P and As, an aliphatic carbocyclic group including at least one of Si, O, S, Se, N, P and As, an aliphatic heterocyclic group including at least one of Si, O, S, Se, N, P and As, and a aromatic heterocyclic group including at least one of Si, O, S, Se, N, P and As.

In accordance with the example embodiments, since the preparation of hydrazine or a derivative thereof, to which carbon dioxide is bonded, uses high-pressure carbon dioxide at from 0.5 MPa to 100 MPa, the carbon dioxide and the hydrazine derivative are rapidly reacted with each other to be easily converted into hydrazine carboxylic acid or a derivative thereof, so that time and energy can be significantly reduced, and furthermore, since residual water in the liquid hydrazine derivative can be minimized, hydrazine or a derivative thereof, to which carbon dioxide is bonded, which rarely generate water and a by-product, can be obtained in a solid or gel form. To the present, such hydrazine or a derivative thereof, to which carbon dioxide is bonded, has been a compound, which could not have been isolated and synthesized to be in a pure solid or gel form, and thus, could not have been clearly specified with respect to the form or structure of the material. In other words, example embodiments can isolate and synthesize hydrazine or a derivative compound thereof, to which carbon dioxide is bonded, and thus, have an effect in clearly identifying the existence of the hydrazine or the derivative compound thereof, and expanding the scope of application of the same.

Compared to liquid hydrazine and derivatives thereof, the powder and gel of hydrazine and its derivative, to which carbon dioxide is bonded, that have been developed in example embodiments provide the following advantages: (i) since the hydrazine and its derivative powder and gel, to which carbon dioxide is bonded, are in a stable solid (gel) state at a room temperature, they are convenient for storage and use and are not hazardous; (ii) since carbon dioxide is easily isolated upon the reaction, they have excellent reactivity like anhydrous hydrazine and a derivative thereof; (iii) the reaction can be accomplished even in an environment with no solvent; (iv) since they contain no water, they can be used in an anhydrous environment; (v) solid state reaction between the solids is possible; and (vi) there is no by-product upon reaction.

In accordance with the example embodiments, since the hydrazine and the derivative compound thereof, to which carbon dioxide is bonded, can be easily used and is safe in industrial fields, economical profits can be obtained, and furthermore, safe conditions for use can be secured. Since the hydrazine and the derivative compound thereof, to which carbon dioxide is bonded, can be used in exact amounts, compared to liquid hydrazine and derivatives thereof, they can be used in the state that their use amounts are exactly adjusted when they are used for fuel or chemical reactions so that generation of a by-product can be minimized.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

Figure 1A:
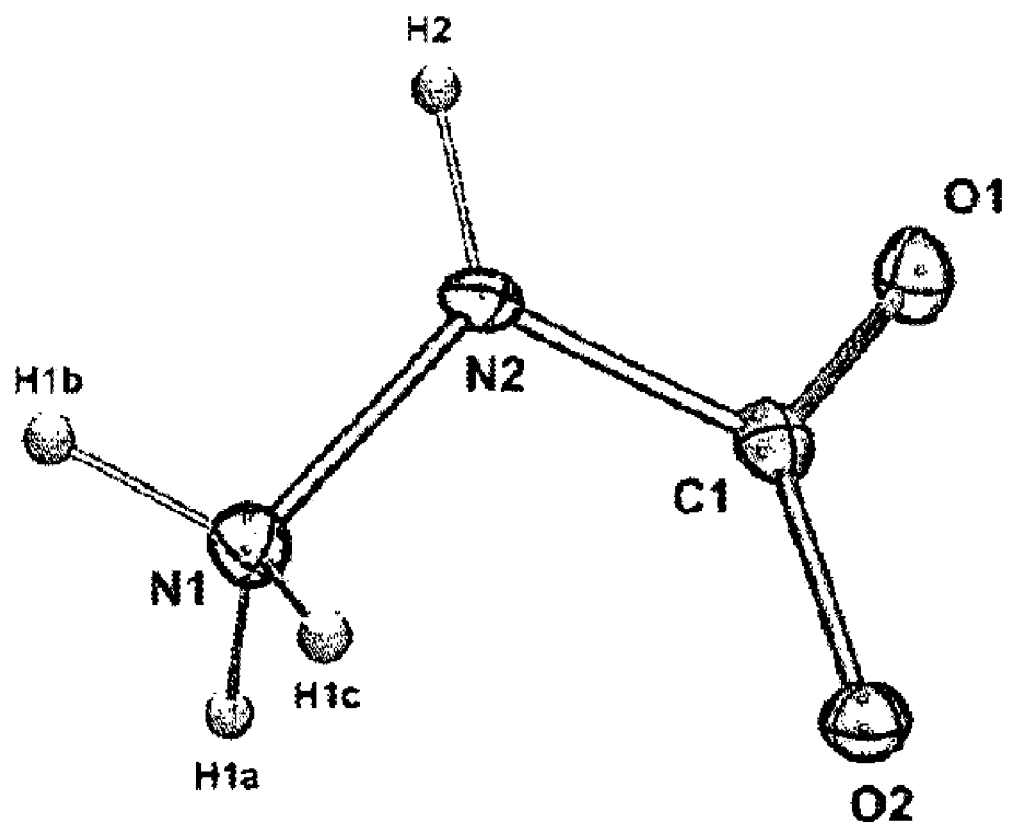
FIG. 1a and FIG. 1b show X-ray crystal structures (ORTEP) of an amphiprotic ionic compound 1, $H_3N^+NHCO_2^-$.

In example embodiments, for quantitative (1:1) reaction of hydrazine and derivatives thereof with carbon dioxide, a compound represented by the following Structural Formula I was reacted with high-pressure carbon dioxide so that hydrazine or a derivative compound thereof, to which carbon dioxide was chemically bonded, and which was represented by the following Structural Formula II, was synthesized. The synthesized compound of Structural Formula II is converted into Structural Formula III at a proper temperature depending on substituents as shown in Reaction Formula I.

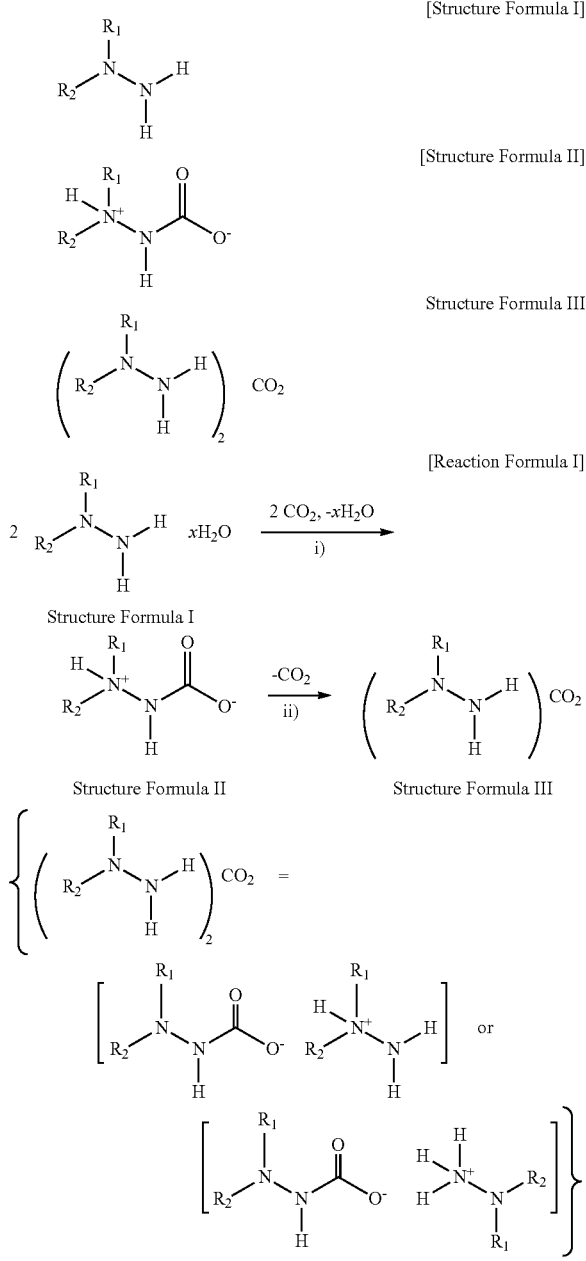

In Structural Formulas I, II and III, each of $R_1$ and $R_2$ is independently hydrogen; or, one of an aliphatic hydrocarbon group of 1 to 30 carbons, a substituted aliphatic hydrocarbon group of 1 to 30 carbons, a substituted aliphatic carbocyclic group of 1 to 30 carbons, a substituted aliphatic heterocyclic group of 1 to 30 carbons, a substituted aromatic cyclic group of 1 to 30 carbons, and a substituted aromatic heterocyclic group of 1 to 30 carbons; or, one of an aliphatic hydrocarbon group including at least one of Si, O, S, Se, N, P and As, an aliphatic carbocyclic group including at least one of Si, O, S, Se, N, P and As, an aliphatic heterocyclic group including at least one of Si, O, S, Se, N, P and As, and a aromatic heterocyclic group including at least one of Si, O, S, Se, N, P and As.

The aliphatic hydrocarbon group may include alkyl, an alkenyl group, and others.

An "alkyl" means a straight- or side-chain non-substituted or substituted saturated hydrocarbon group, and may include, for example, methyl, ethyl, propyl, isopropyl, isobutyl, sec butyl, tert butyl, pentyl, hexyl, heptyl, octyl, nonyl, decyl, undecyl, tridecyl, pentadecyl, heptadecyl, and others. $C_1$-$C_{10}$ alkyl means an alkyl group having an alkyl unit of 1 to 10 carbons, and does not include the number of carbons of a substituent when the $C_1$-$C_{10}$ alkyl is substituted. When alkyl is substituted, it may be substituted at various positions by various substituents, e.g., halo, hydroxyl, nitro, cyano, $C_1$-$C_4$ substituted or non-substituted straight- or branch-chain alkyl, $C_1$-$C_4$ straight- or branch-chain alkoxy or alkylcarboxylnitro.

An "alkenyl" means a straight- or branch-chain non-substituted or substituted unsaturated hydrocarbon group having a designated number of carbons, and may include, for example, ethenyl, vinyl, propenyl, allyl, isopropenyl, butenyl, isobutenyl, t-butenyl, n-pentenyl, and n-hexenyl. When alkenyl is substituted, it may be substituted at various positions by various substituents, e.g., halo, hydroxy, nitro, cyano, $C_1$-$C_4$ substituted or non-substituted straight- or branch-chain alkyl, $C_1$-$C_4$ straight- or branch-chain alkoxy, or alkylcarboxylnitro.

The aromatic cyclic group or the substituted aromatic heterocyclic group may include aryl, hetero aryl, aryl alkyl, a fused aryl group, and others.

An "aryl" means a completely or partially unsaturated substituted or non-substituted monocyclic or polycyclic carbocyclic group. $C_6$-$C_{30}$ aryl means an aryl group having a carbocyclic atom of 6 to 30 carbons, and does not include the number of carbons of a substituent when the $C_6$-$C_{30}$ aryl is substituted. Preferably, aryl is monoaryl or biaryl. Monoaryl preferably has 5 to 6 carbons, and biaryl preferably has 9 to 10 carbons. Most preferably, the aryl is substituted or non-substituted penyl. When monoaryl, e.g., penyl is substituted, the substitution may occur at various positions by various substituents, e.g., halo, hydroxy, nitro, cyano, $C_1$-$C_4$ substituted or non-substituted straight- or branch-chain alkyl or $C_1$-$C_4$ straight- or branch-chain alkoxy.

A "heteroaryl" is a heterocyclic aromatic group, and may include Si, O, S, Se, N, P or As as a hetero atom. $C_3$-$C_{30}$ heteroaryl means a heteroaryl group having a carbocyclic atom of 3 to 30 carbons, and does not include the number of carbons of a substituent when the $C_3$-$C_{30}$ heteroaryl is substituted. The number of the hetero atoms is preferably 1 to 2. In the heteroaryl, aryl is preferably monoaryl or biaryl, and most preferably, monoaryl. The heteroaryl may be substituted at various positions by various substituents, e.g., halo, hydroxyl, nitro, cyano, $C_1$-$C_4$ substituted or non-substituted straight- or branch-chain alkyl, or $C_1$-$C_4$ straight- or branch-chain alkoxy.

An "arylalkyl" means an alkyl group substituted with an aryl group. $C_6$-$C_{30}$ arylalkyl means arylalkyl having an arylalkyl unit having 6 to 30 carbons, and does not include the number of carbons of a substituent when the $C_6$-$C_{30}$ arylalkyl is substituted. In the arylalkyl, aryl is preferably monoaryl or biaryl, and alkyl is preferably $C_1$-$C_3$ alkyl, and more preferably, $C_1$ alkyl. In the arylalkyl, aryl may be substituted at various positions by various substituents, e.g., halo, hydroxyl, nitro, cyano, $C_1$-$C_4$ substituted or non-substituted straight- or branch-chain alkyl, $C_1$-$C_4$ straight- or branch-chain alkoxy or alkylcarboxylnitro.

A "fused aryl group" means a ring form consisting of fused multiple aryl rings, and may include naphthalene, phenanthrene, anthracene, benzo[a]pyrene, benzo[b]pyrene, benzo[e]pyrene, acenaphthalene, acenaphthene, benzo[b]fluoranthene, benzo[j]fluroranthene, chrysene, fluoranthene, fluorene, pyrene, and others, which are substituted or non-substituted fused aryl groups. The fused aryl group may be substituted at various positions by various substituents, e.g., halo, hydroxy, nitro, cyano, $C_1$-$C_4$ substituted or non-substituted straight- or branch-chain alkyl, or $C_1$-$C_4$ straight- or branch-chain alkoxy.

The reaction in the high-pressure condition may be accomplished under a solvent-free condition or under water, an alcohol of $C_1$-$C_{12}$, an ether of $C_2$-$C_{12}$, or a mixed solvents thereof. Especially, when the reaction is accomplished under an alcohol solvent of $C_1$-$C_{12}$, hydrazine carboxylic acid or a derivative thereof having higher purity can be obtained.

When an alcohol is used as a solvent, the solvent may include methanol, ethanol, propanol, isopropanol, n-butanol, isobutanol, sec-butanol, tert-butanol, n-pentanol, isopentanol, sec-pentanol, tert-pentanol, hexanol, heptanol, octanol, nonanol, decanol, undecanol, dodecanol, pentadecanol, and others, but may not be limited thereto. The solvent may include polyol such as ethyleneglycol, glycerol, erythritol, xylitol, and mannitol, but may not be limited thereto.

When an ether is used as a solvent, the solvent may include dimethylether, diethylether, THF, dioxin, and others, but may not be limited thereto.

A temperature in the reaction of the high-pressure condition may be adjusted to be from –20° C. to 300° C. This is because the reaction would not be normally accomplished at a temperature of –20° C. or less, and significant improvement in a reaction velocity cannot be achieved when the temperature exceeds 300° C.

A water content of the hydrazine derivative hydrate may be from 1 wt % to 99 wt %, more preferably, from 10 wt % to 80 wt %.

For the carbon dioxide, vapor or liquid carbon dioxide, and furthermore, carbon dioxide in the supercritical state or a solid-state dry ice may be used.

A step of reducing the pressure to from 0.01 MPa to 0.1 MPa to vaporize excess carbon dioxide may be added after the reaction in the high-pressure condition.

A certain amount of water existing in the reactant (hydrazine or a derivative thereof) in Step i) is isolated when the compound of Structural Formula II is produced. The pressure in the reaction of Step i) is preferably from 0.3 MPa to 100 MPa, and when the pressure is adjusted to 0.3 MPa or less, the reaction of carbon dioxide and the liquid hydrazine derivative occurs, but a sticky precipitate in a gel form is gradually generated and is not produced in a powder form. The sticky property of the precipitate remains even when the precipitate is washed with alcohol several times and dried in vacuum. In this case, when the reactant is hydrazine ($R_1$=$R_2$=H in Structural Formula I), the solid product having viscosity due to the existing water is present as a mixture consisting of carbazic acid and hydrazinium carbazate, through the route of the following Reaction Formula 2, and accordingly, is not purely isolated in the form of the following Structural Formula II. Thus, the product has not been reported so far.

[Reaction Formula 2]

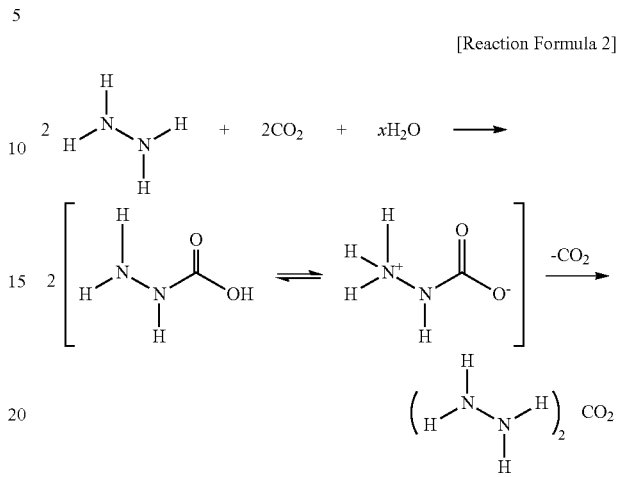

Figure 1B:
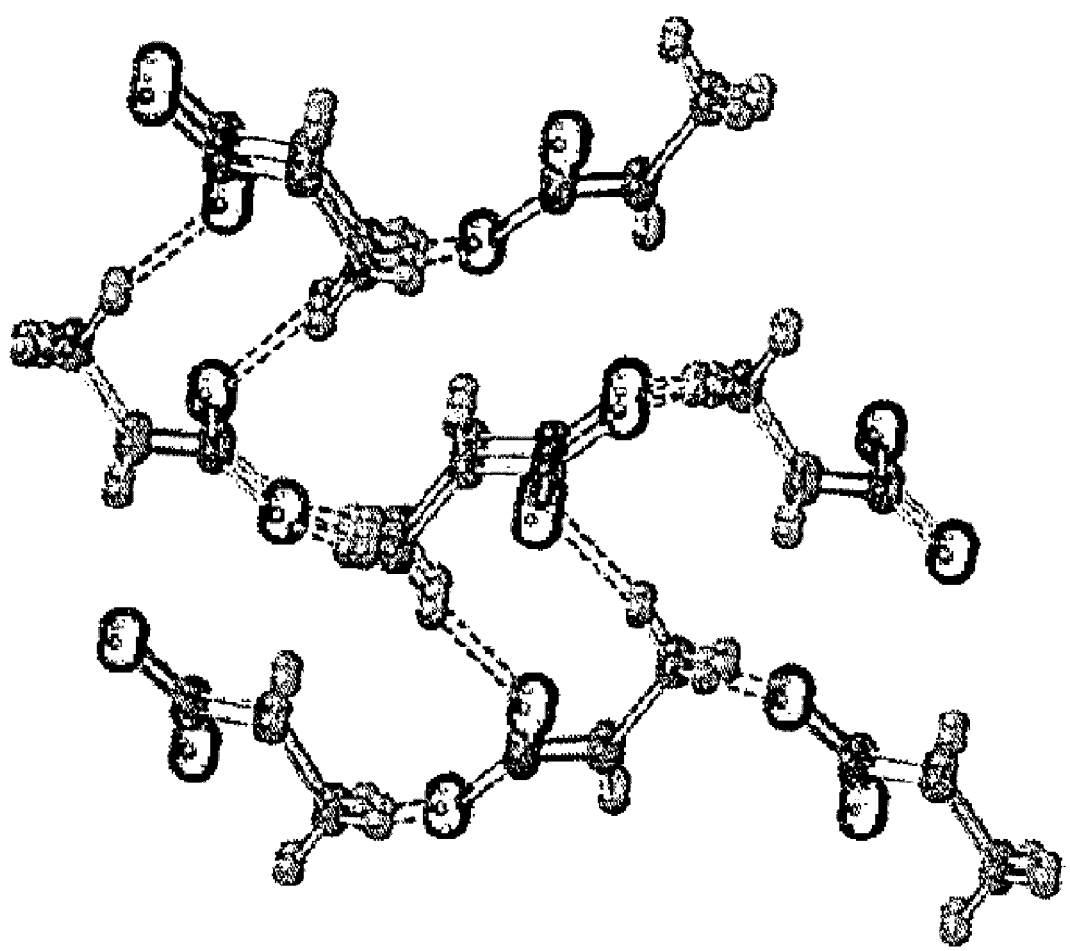
Figure 2A:
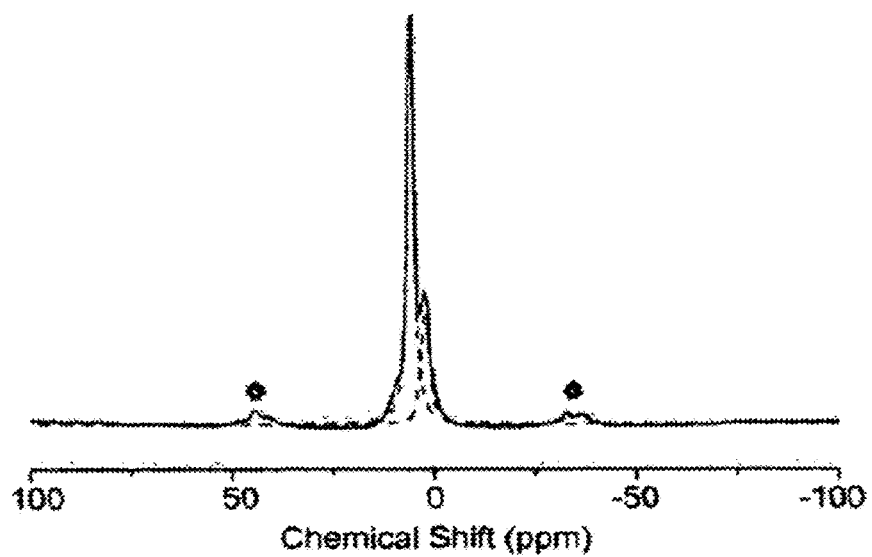
FIG. 2a and FIG. 2b show a solid state $^1$H-NMR peak and a $^{13}$C NMR peak of an amphiprotic ionic compound 1, $H_3N^+NHCO_2^-$.
Figure 2B:
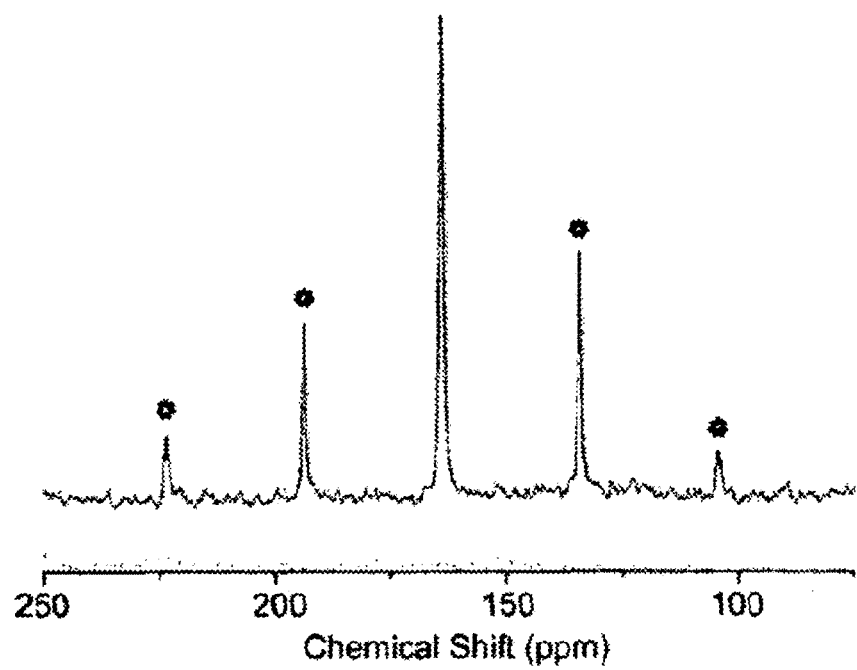
Figure 3:
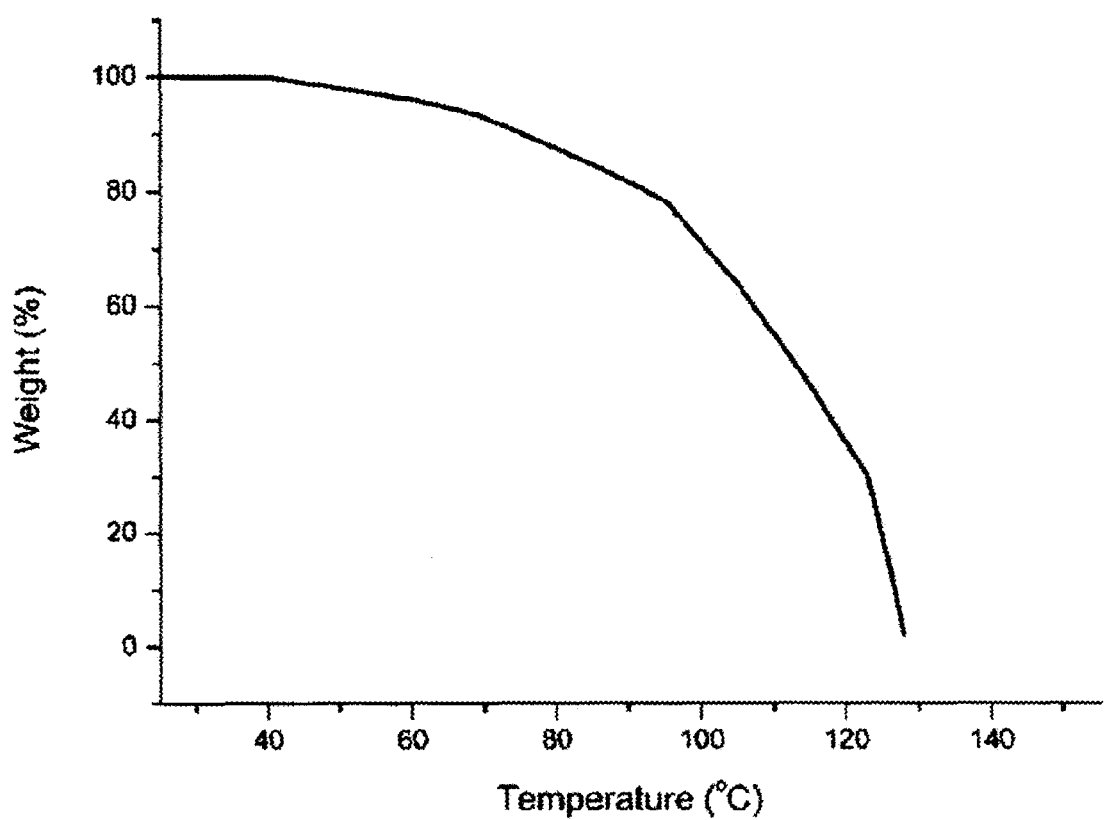
FIG. 3 shows solid state TGA/DSC of an amphiprotic ionic compound 1, $H_3N^+NHCO_2^-$.
Figure 4:
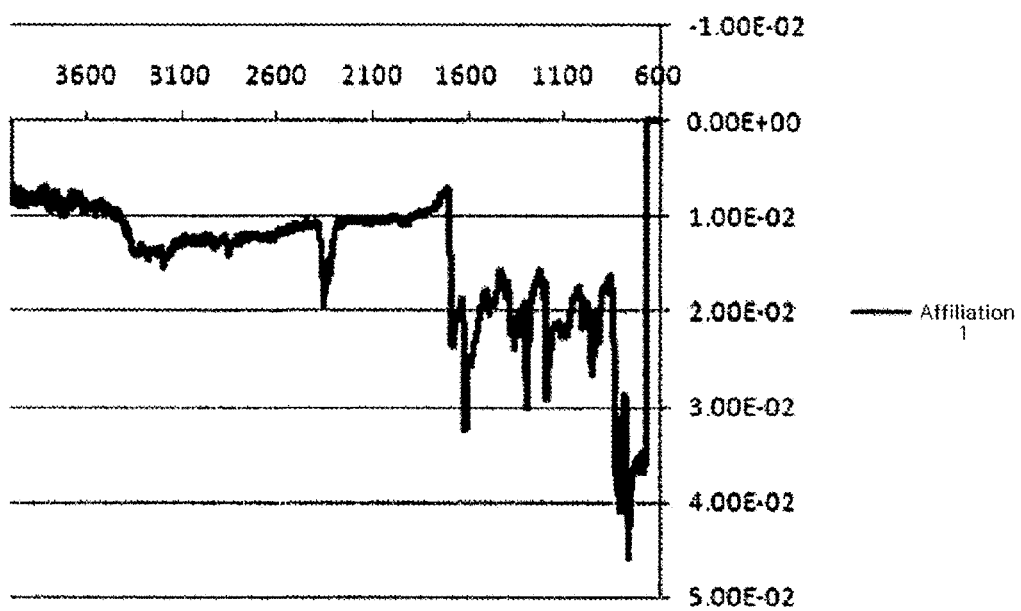
FIG. 4 shows a solid state IR spectrum of an amphiprotic ionic compound 1, $H_3N^+NHCO_2^-$.
Figure 5:
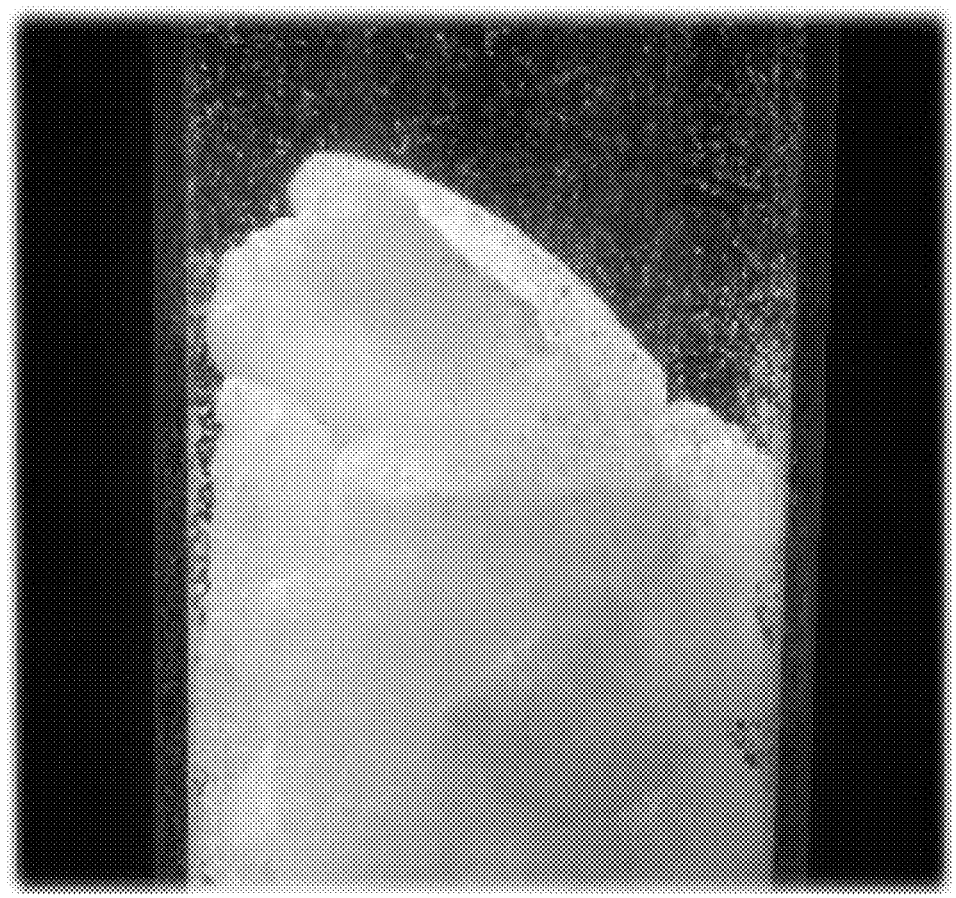
FIG. 5 shows a photograph of an amphiprotic ionic compound 1, $H_3N^+NHCO_2^-$, which is produced in a crystal form.

However, in the high-pressure carbon dioxide condition, hydrazine and carbon dioxide very rapidly react with each other, and a compound of the following Structural Formula II is quantitatively produced. The produced compound of Structural Formula II is clearly isolated from water present in the reaction mixture, and thus, the material of Structural Formula II as a product is no longer changed in the reaction condition. That is, the equilibrium represented in Reaction Formula 2 does not occur. Such an amphiprotic ionic compound 1 (hydrazinium carboxylate) have never been reported until the present disclosure, and has been merely suggested as a carbazic acid structure. The aforementioned descriptions have been recently published in a document by the inventors of the present disclosure (Lee, B.; Kang, S. H.; Kang, D. Lee, K. H.; Cho, J.; Nam, W. Han O. H.; Hur, N. H. *Chem. Commun.*, 2011, 47, 1121911221). FIG. 1a and FIG. 1b show a crystal structure of the compound of Structure Formula II, FIG. 2 shows $^1$H and $^{13}$C NMR (nuclear magnetic resonance) spectra of the solid state, FIG. 3 shows TGA/DSC (thermogravimetric analyzer/differential scanning calorimetry) data, FIG. 4 shows an IR (infrared ray) spectrum, and FIG. 5 shows a photograph of the solid state.

[Structural Formula II]

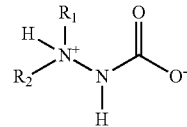

When this compound is heated, a compound in a gel form, i.e., $R_1$=$R_2$=H in Structure Formula III, is produced in the anhydrous state.

In addition, the compounds of $R_1$=$CH_3$, Ph, 1-Pyridyl, $HOCH_2CH_2$, $R_2$=H, and others are produced and isolated to be in the form of Structural Formula II. Although most of the compounds exist in a white solid form at a low temperature (<4° C.), they may lose part of the carbon dioxide at a high temperature and be converted into the form of Structural Formula III. The compounds exhibit different properties depending on substituents represented by $R_1$, but maintain the form of Structure Formula II or III. Those compounds have not been known.

Since the above-described compounds of Structure Formulas II and III do not use a solvent, they offer superior advantages in that each of the compounds is reacted with one (1) and two (2) equivalent weights of carbonyl compounds in a highly eco-friendly condition to produce an imine or azine compound with a selectively high yield rate (~100%) (refer to the following Reaction Formulas 3 to 5). Further, there is an advantage in that since carbon dioxide and water, which are by-products of the reaction, are treated as materials not causing pollution and removed into the air during the reaction, a separate isolation process is unnecessary. However, the compounds of Structural Formula I, which do not react with carbon dioxide, do not exhibit the superior property of the compounds of Structural Formulas II and III, which are obtained in the example embodiments, under the similar condition to that for the compounds of Structural Formulas II and III.

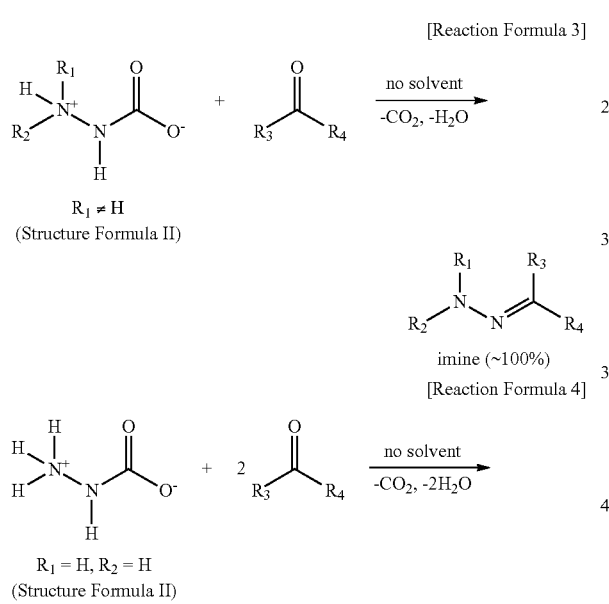

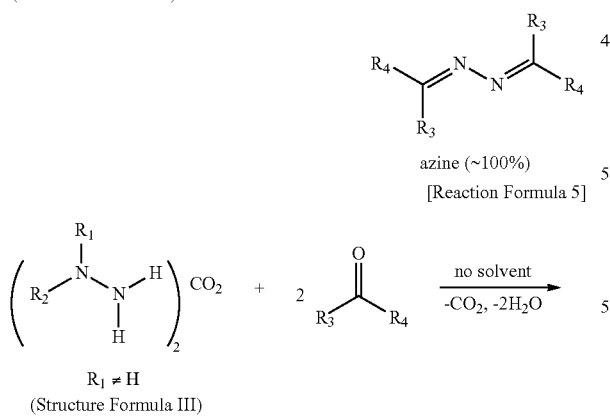

Meanwhile, if $R_1$ and $R_2$ are alkyl, i.e., a saturated or unsaturated aliphatic hydrocarbon group like 1,1-dimethyl-hydrazine ($R_1$=$R_2$=$CH_3$), they are produced in the form of Structural Formula II when reacting with carbon dioxide at a low temperature (<0° C.), but have significantly stronger sublimation than other derivatives. Further, the compound of Structural Formula II is immediately changed into the form of Structural Formula III at a temperature of 0° C. or higher, and the associated compound of Structural Formula III loses one ammonium ($NH_3$) molecule and is finally changed into the form of the following Structure Formula IV (refer to Reaction Formula 6). In Structural Formula IV, the compound of $R_1$=$R_2$=$CH_3$ is very stable, and thus, can be grown to be a crystal (refer to FIG. 19).

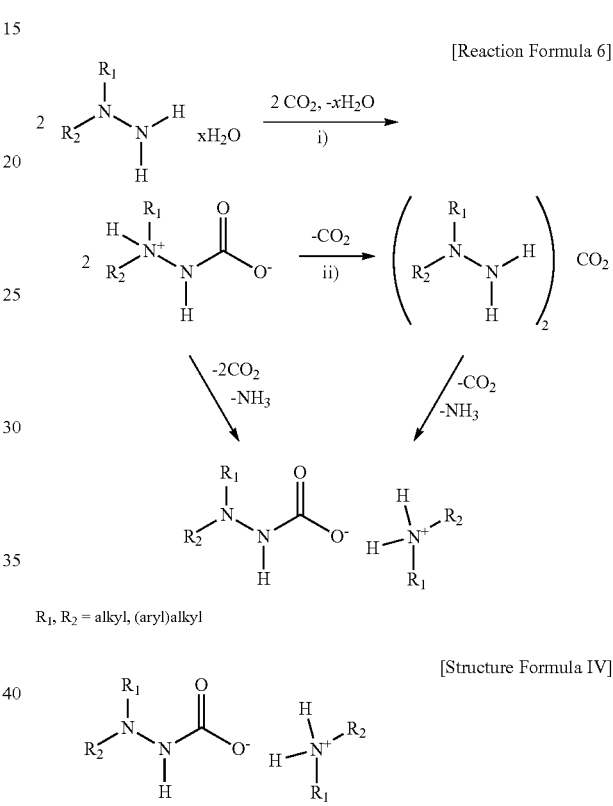

The compound having the form of Structural Formula IV is also subject to 1:1 reaction with a carbonyl compound even under a solvent-free condition as in Reaction Formula 3 to quantitatively produce an imine compound. However, dialkylamine [or di(aryl)alkylamine] is additionally generated as a by-product. However, in case of $R_1$=$R_2$=$CH_3$, since dimethylamine also has a low boiling point, a separate isolation process is unnecessary (refer to the following Reaction Formula 7). That is, by using a material, which generates amine ($R_1R_2NH$) having a low boiling point, imine can be produced without a separate isolation process as shown below.

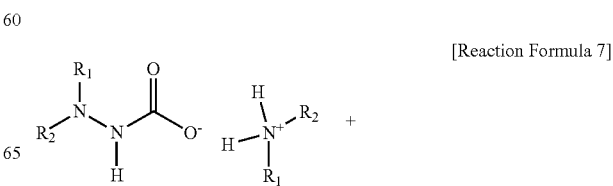

-continued

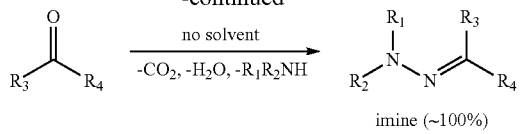

Hereinafter, example embodiments are described in more detail by using Examples. The Examples are merely intended to more specifically describe example embodiments, and it is obvious to one of ordinary skill in the art that the scope of example embodiments is not limited to the Examples, according to the technical gist of example embodiments.

The compounds of Structural Formula I were synthesized according to the descriptions in Korean Patent Application No. 10-2010-0135935 and a method similar thereto, and the compounds of Structural Formula III were synthesized and analyzed based on the compound of Structural Formula II by changing a temperature under the presence of an inert gas.

Example 1

Hydrazinium carboxylate ($H_3N^+NHCO_2^-$, HC) was prepared by putting a 3 g hydrazine hydrate solution having a water content of about 36 wt % into a reactor, and adjusting a pressure of carbon dioxide and a temperature of the reactor. The reaction occurred in the state that the pressure of carbon dioxide was 7.4 MPa or higher, and the temperature was 50° C. The pressure was reduced after the reaction, residual carbon dioxide was vaporized, and the remaining solid was washed with 20 mL methanol five (5) times and dried in vacuum for three (3) times so that a hydrazinium carboxylate crystal was obtained.

As a result of analysis through X-ray crystallography, the crystal was a compound represented by hydrazinium carboxylate ($H_3N^+NHCO_2^-$). A yield rate of $H_3N^+NHCO_2^-$ obtained based on used hydrazine hydrate was 98% or more. FIG. 1 shows the X-ray crystal structure (ORTEP and a packing diagram), and FIG. 2 shows $^1H$, $^{13}C$ NMR in the solid state. NMR materials for the solution state were not measured since there was no proper solvent that can melt the solid. FIG. 3 and FIG. 4 show TGA/DSC and an IR spectrum, respectively. FIG. 5 shows a photograph of the crystalline product.

Results of Elemental Analysis (Unit %) for the Product $H_3N^+NHCO_2^-$

Elements (calculation values, experimental values): C (15.79, 15.75), H (5.30, 5.31), N (36.84, 36.90).

Mass spectrometry MS (EI+) m/z=32 [M]+, 31, 29, 17, 15

Example 2

While using the same method as that of Example 1, the reaction was completed by using dry ice, which is solid carbon dioxide, as a supply source of carbon dioxide. After a 3 g hydrazine hydrate solution having a water content of about 36 wt % was put into a reactor, and the reactor was filled with about 15 g dry ice, the reactor was put into an oil bath set to a temperature of about 100° C. to be reacted. At this time, a pressure was about from 10 MPa to 12 MPa, and under the condition, the reaction occurred for about two (2) hours. The other conditions were the same as those of Example 1. A yield rate of $H_3N^+NHCO_2^-$ obtained based on used hydrazine hydrate was 98% or higher. The same analysis results as those in Example 1 were obtained.

Example 3

The reaction occurred at a temperature of 0° C., and the other conditions and the analysis results were also the same as those of Example 1.

Example 4

The same method as that of Example 1 was used, except for using 1.90 g 1-methyl hydrazine, instead of hydrazine hydrate.

As a result of analysis, in terms of a structural formula, the powder was a compound represented by 2-methyl hydrazinium carboxylate [$(CH_3)H_2N^+NHCO_2^-$]. A yield rate of $(CH_3)H_2N^+NHCO_2^-$ obtained based on used 1-methyl hydrazine was 94% (3.50 g) or more.

Results of Elemental Analysis (Unit %) for the Product $(CH_3)H_2N^+NHCO_2^-$

Elements (calculation values, experimental values): C (26.66, 26.57), H (6.71, 6.76), N (31.10, 30.96).

$^1H$ NMR (400 MHz, $CD_3OD$, 27° C.) δ 4.96 (br. s, 2H, —NH & —N$^+$H$_2$), 2.68 (br. s, 3H, $CH_3$); $^{13}C$ NMR (100 MHz, $CD_3OD$, 27° C.) δ 38.0 ($CH_3$), 160.1 (C=O).

Figure 6:
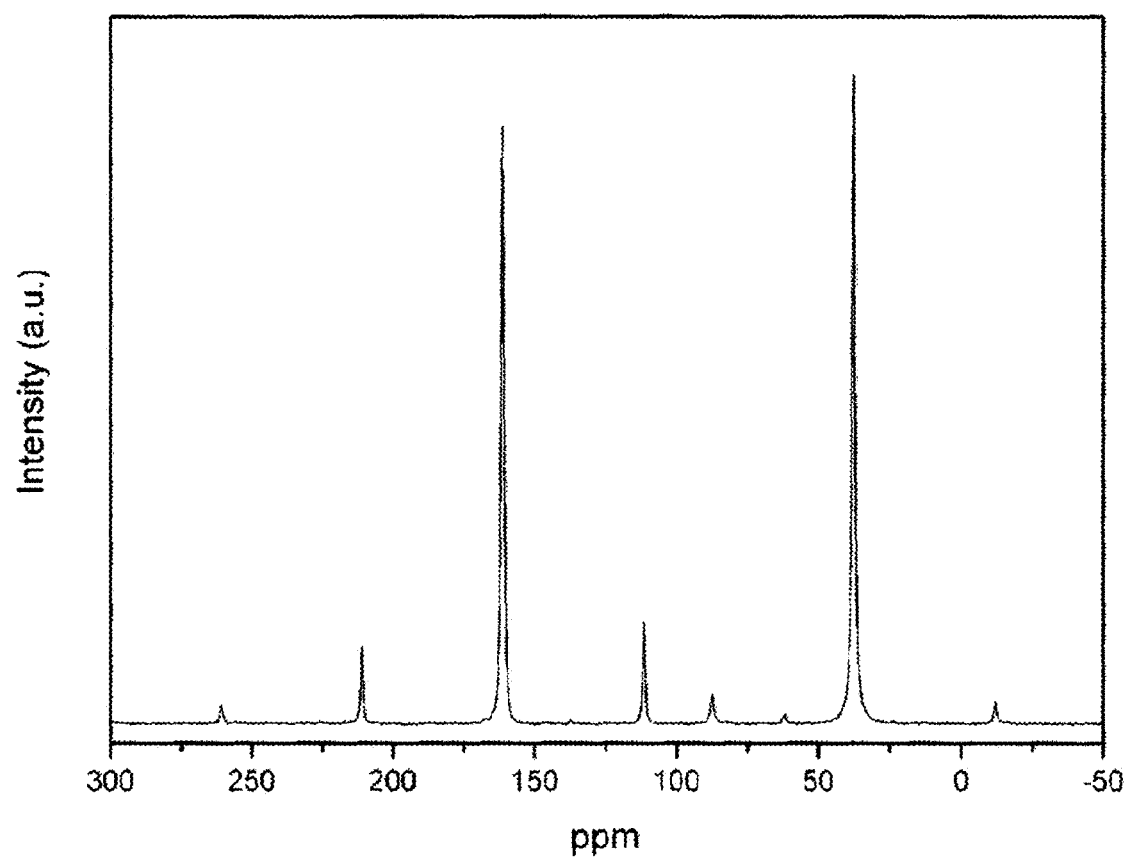
FIG. 6 is a solid-state $^{13}$C-NMR spectrum of a $(CH_3)H_2N^+NHCO_2^-$ compound.
Figure 7:
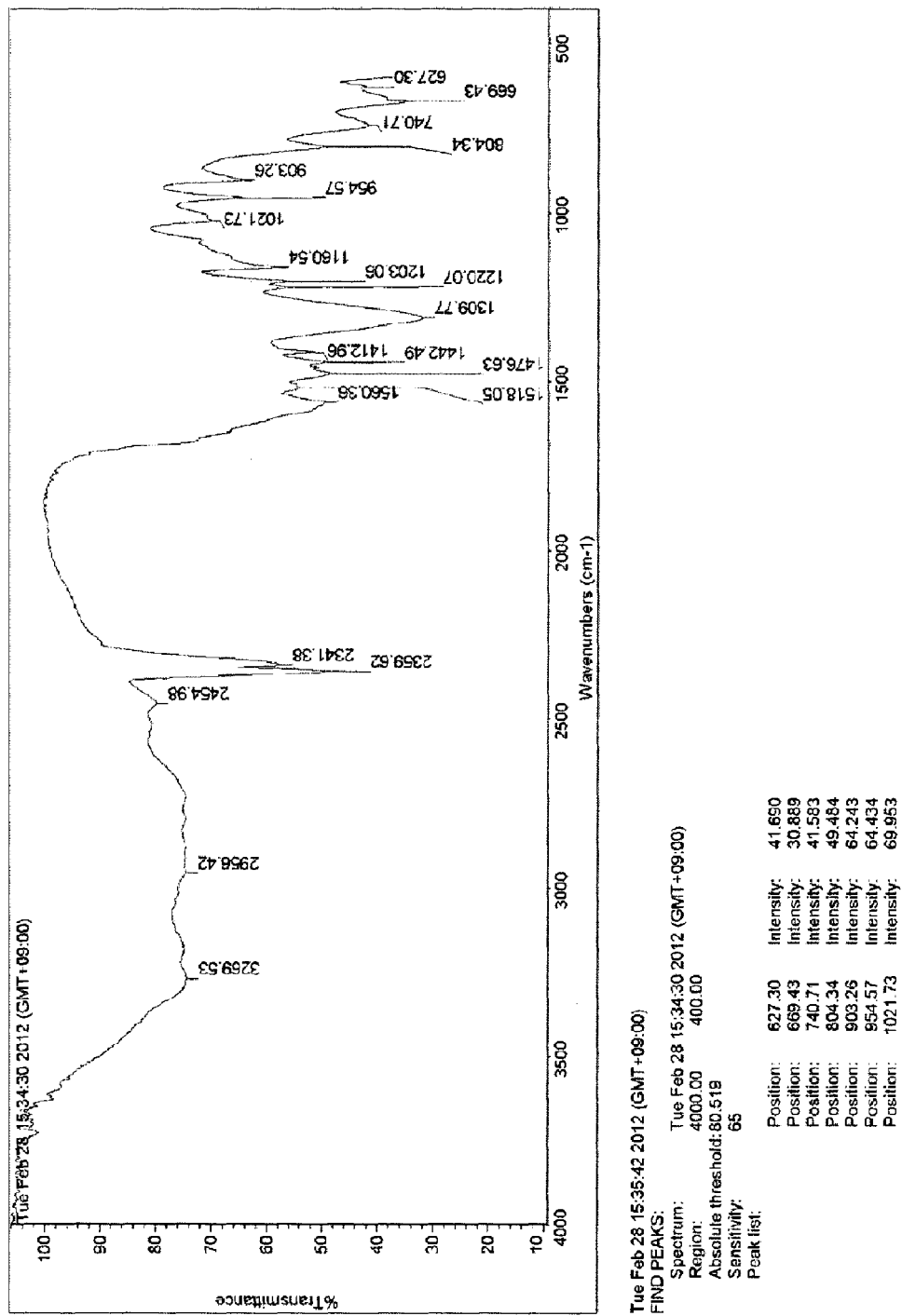
FIG. 7 shows an IR spectrum of a $(CH_3)H_2N^+NHCO_2^-$ compound.
Figure 8:
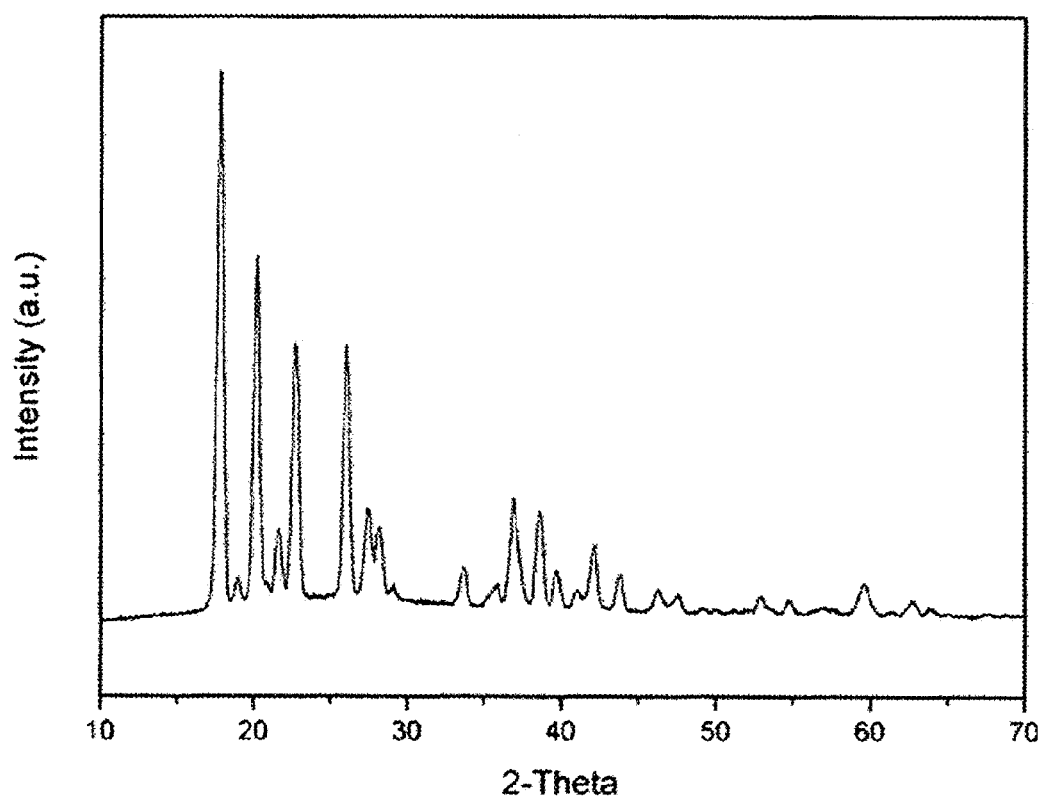
FIG. 8 shows XRD data for a $(CH_3)H_2N^+NHCO_2^-$ compound.

This compound was also analyzed by solid $^{13}C$ NMR, and FIG. 6 shows a spectrum thereof. FIG. 7 and FIG. 8 show an IR spectrum and XRD (X-ray diffraction) data for the $(CH_3)H_2N^+NHCO_2^-$ compound liquefied at a room temperature, respectively.

Example 5

The same method as that of Example 1 was used, except for using 2.16 g 1-phenyl hydrazine, instead of hydrazine hydrate.

As a result of analysis, in terms of a structural formula, the powder was a compound represented by 2-phenyl hydrazinium carboxylate [$H_2(C_6H_5)N^+NHCO_2^-$]. A yield rate of $H_2(C_6H_5)N^+NHCO_2^-$ obtained based on used 1-phenyl hydrazine was 96% (2.92 g) or more.

Results of Elemental Analysis (Unit %) for the Product $H(C_6H_5)N^+NHCO_2^-$

Elements (calculation values, experimental values): C (55.26, 55.05), H (5.30, 5.21), N (18.41, 18.57).

$^1H$ NMR (400 MHz, $CD_3OD$, 27° C.) δ 4.87 (br. s, 3H, N—H & N$^+$—H$_2$) 6.75 (t, J=7.2 Hz, 1H, phenyl), 6.85 (t, J=7.6 Hz, 2H, phenyl), 7.17 (m, 2H); $^{13}C$ NMR (100 MHz, $CD_3OD$, 27° C.) δ 112.3, 118.9, 128.5, 151.4 (phenyl), 158.2 (C=O)

mp=78° C.

Figure 9:
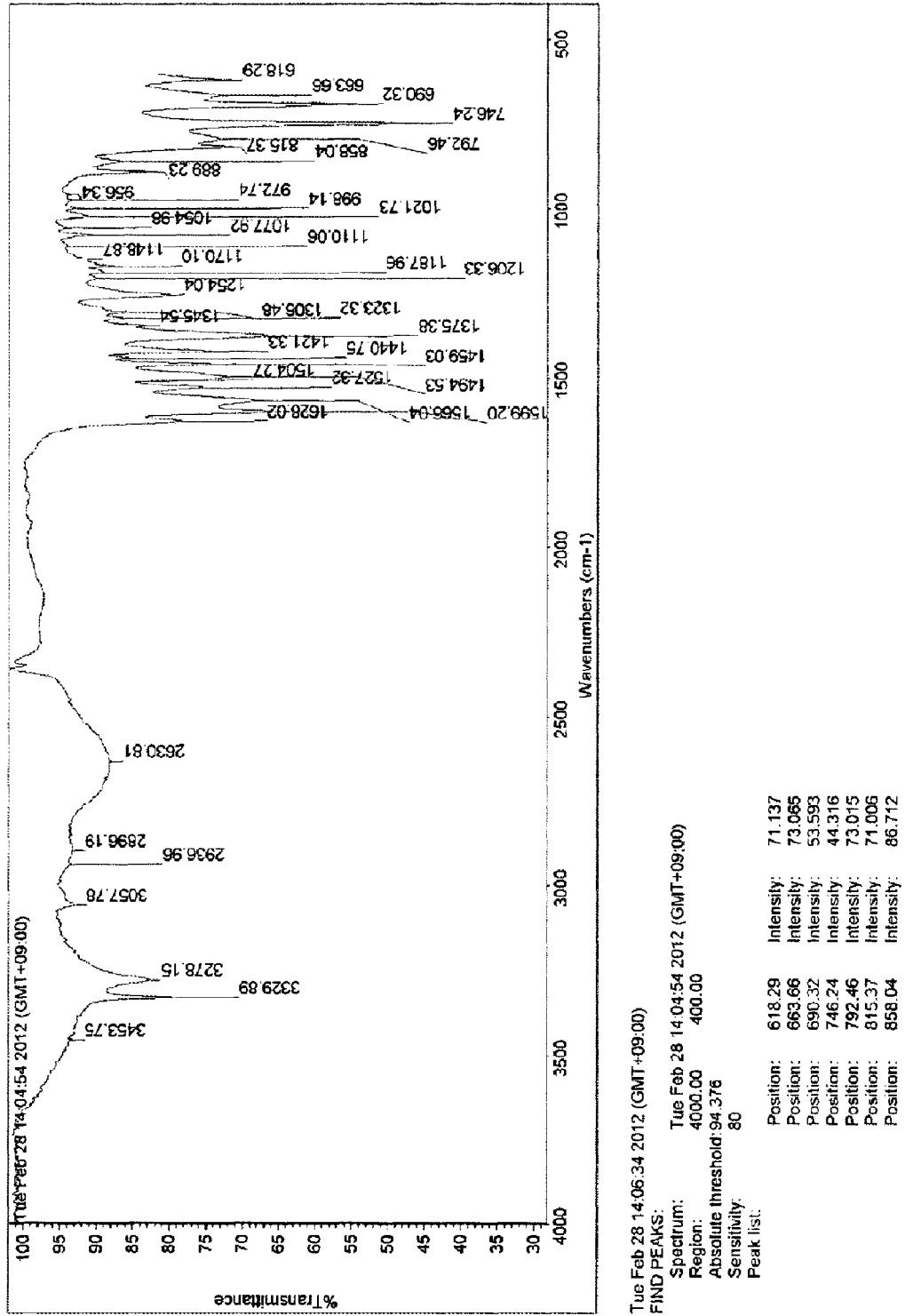
FIG. 9 shows an IR spectrum for a $H(C_6H_5)N^+NHCO_2^-$ compound.
Figure 10:
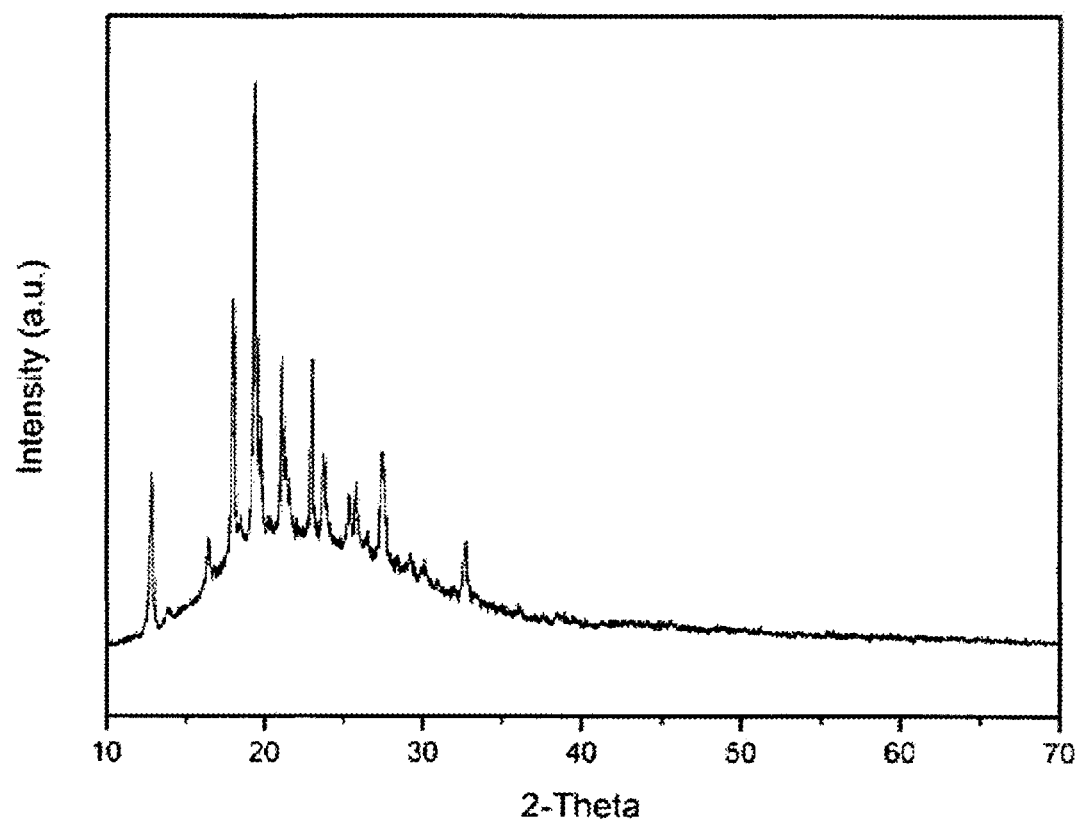
FIG. 10 shows XRD data for a $H(C_6H_5)N^+NHCO_2^-$ compound.

FIG. 9 and FIG. 10 show an IR spectrum and XRD data for the compound, respectively.

Example 6

The same method as that of Example 1 was used, except for using 2.2 g 2-hydrazinylpyridine, instead of hydrazine hydrate.

As a result of analysis, in terms of a structural formula, the powder was a compound represented by 2-(pyridin-2-yl) hydrazinium carboxylate, [$H_2(2-C_3H_4N)N^+NHCO_2^-$]. A yield rate of $H_2(2-C_3H_4N)N^+NHCO_2^-$ obtained based on used 2-hydrazinylpyridine was 95% (2.91 g) or more.

Results of Elemental Analysis (Unit %) for the Product $H_2(2-C_3H_4N)N^+NHCO_2^-$ Elements (calculation values, experimental values): C (47.06, 47.21), H (4.61, 4.11), N (27.44, 27.23).

$^1$H NMR (400 MHz, CD$_3$OD, 27° C.) δ 4.89 (br. s, 3H, N—H & N$^+$—H$_2$) 6.60 (m, 1H, pyridyl), 6.78 (m, 1H, pyridyl), 7.46 (m, 1H, pyridyl), 7.98 (m, 1H, pyridyl); $^{13}$C NMR (100 MHz, CD$_3$OD, 27° C.) δ 107.2, 113.4, 137.5, 137.7, 146.5 (pyridyl), 161.6 (C═O)

mp=56° C.

Figure 11:
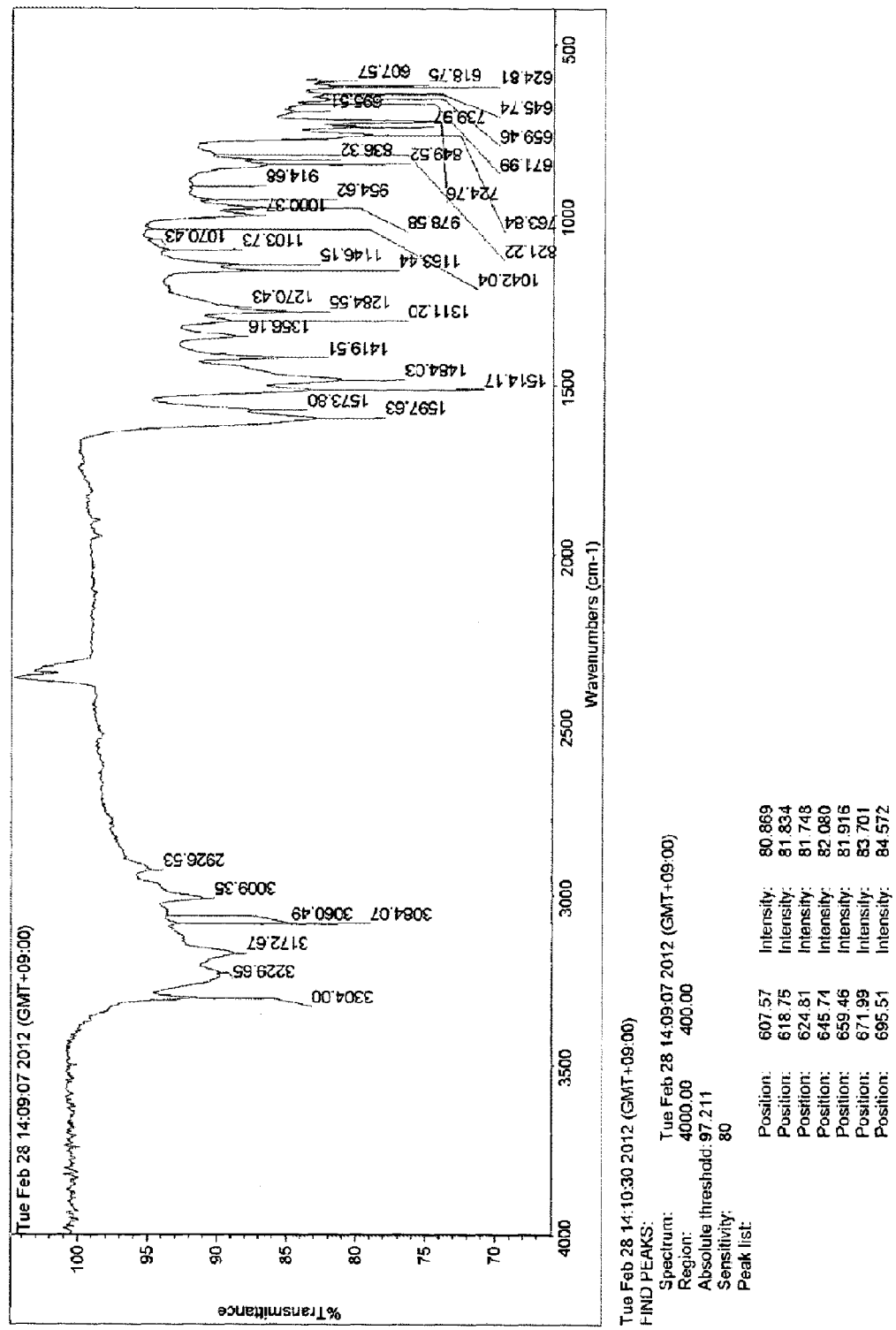
FIG. 11 is an IR spectrum for a $H_2(2-C_5H_4N)N^+NHCO_2^-$ compound.
Figure 12:
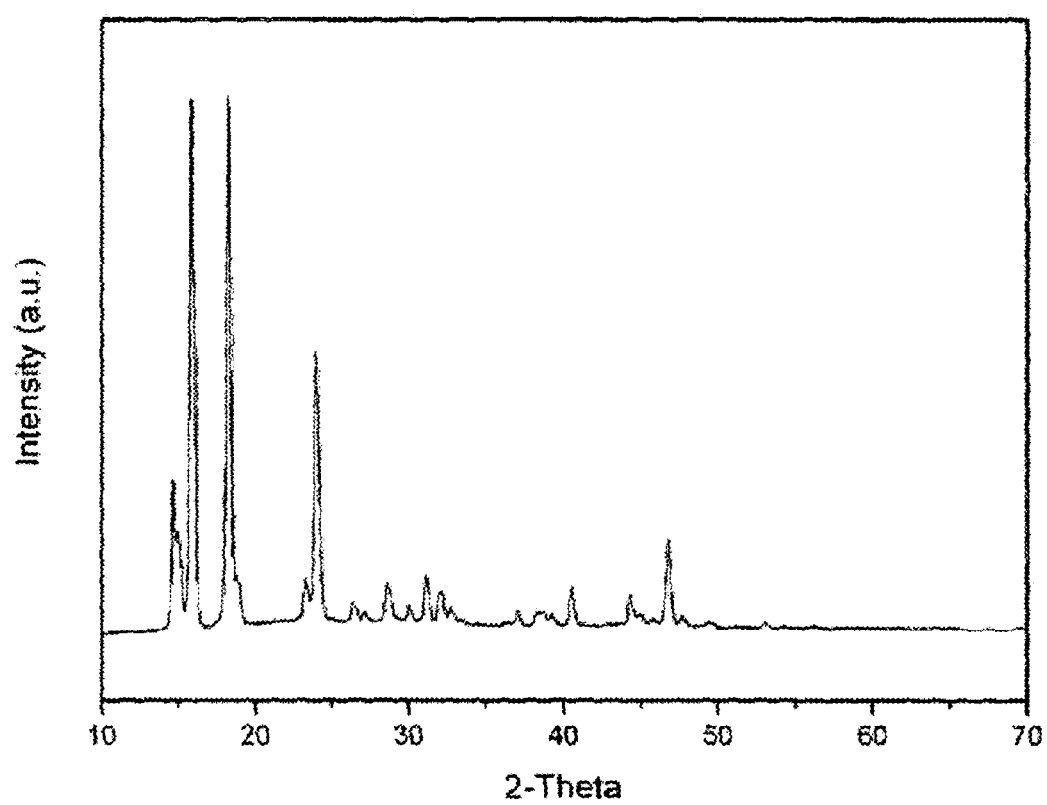
FIG. 12 shows XRD data for a $H_2(2-C_5H_4N)N^+NHCO_2^-$ compound.

FIG. 11 and FIG. 12 show an IR spectrum and XRD data for the compound, respectively.

Example 7

The same method as that of Example 1 was used, except for using 1.53 g 2-hydrazinoethanol, instead of hydrazine hydrate.

As a result of analysis, in terms of a structural formula, the powder was a compound represented by 2-(2-hydroxyethyl) hydrazinium carboxylate [(HOCH$_2$CH$_2$)H$_2$N$^+$NHCO$_2$$^-$]. A yield rate of (HOCH$_2$CH$_2$)H$_2$N$^+$NHCO$_2$$^-$ obtained based on 2-hydrazinoethanol was 94% (2.26 g) or more.

Results of Elemental Analysis (Unit %) for the Product (HOCH$_2$CH$_2$)H$_2$N$^+$NHCO$_2$$^-$ Elements (calculation values, experimental values): C (30.00, 29.57), H (6.71, 6.86), N (23.32, 23.71).

$^1$H NMR (400 MHz, CD$_3$OD, 27° C.) δ 2.90 (br. s, 2H, CH$_2$—N), 3.70 (br. s, 2H, CH$_2$—OH), 4.98 (m, 3H, OH, —NH & —N$^+$H$_2$); $^{13}$C NMR (100 MHz, CD$_3$OD, 27° C.) δ 55.1 (CH$_2$—N), 58.4 (CH$_2$—O), 164.6 (C═O).

Figure 13:
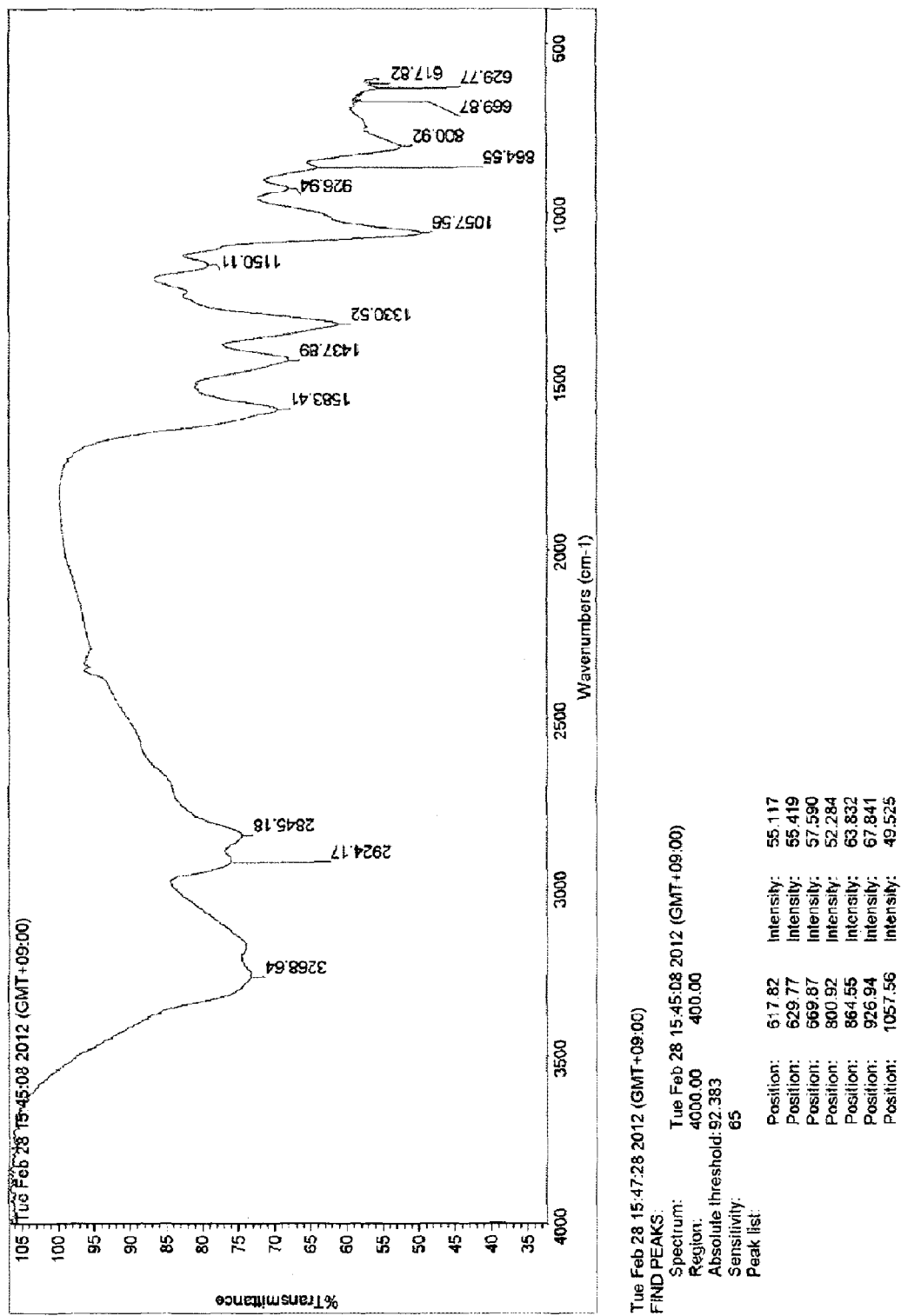
FIG. 13 shows an IR spectrum for a $(HOCH_2CH_2)H_2N^+NHCO_2^-$ compound.

FIG. 13 shows an IR spectrum of the compound.

Example 8

The same method as that of Example 1 was used, except for using 1.23 g 1-methyl 1-phenyl hydrazine, instead of hydrazine hydrate.

As a result of elemental analysis, in terms of a structural formula, the powder was a compound represented by 2-methyl-2-phenyl hydrazinium carboxylate [H(CH$_3$)(C$_6$H$_5$)N$^+$NHCO$_2$$^-$]. A yield rate of H(CH$_3$)(C$_6$H$_5$)N$^+$NHCO$_2$$^-$ obtained based on used 1-methyl-1-phenyl hydrazine was 93% (1.55 g) or more.

Results of Elemental Analysis (Unit %) for the Product H(CH$_3$)(C$_6$H$_5$)N$^+$NHCO$_2$$^-$ Elements (calculation values, experimental values): C (57.82, 58.01), H (6.07, 6.01), N (16.86, 16.79).

$^1$H NMR (400 MHz, CDCl$_3$, 27° C.) δ 3.13 (s, 3H, CH$_3$), 3.68 (br. s, 2H, NH & N$^+$H), 6.93 (m, 1H, phenyl), 7.10 (m, 2H, phenyl), 7.37 (m, 2H, phenyl), $^{13}$C NMR (100 MHz, CDCl$_3$, 27° C.) δ 41.7 (CH$_3$—N), 112.6, 117.2, 129.4, 149.8 (phenyl), 162.1 (C═O).

Figure 14:
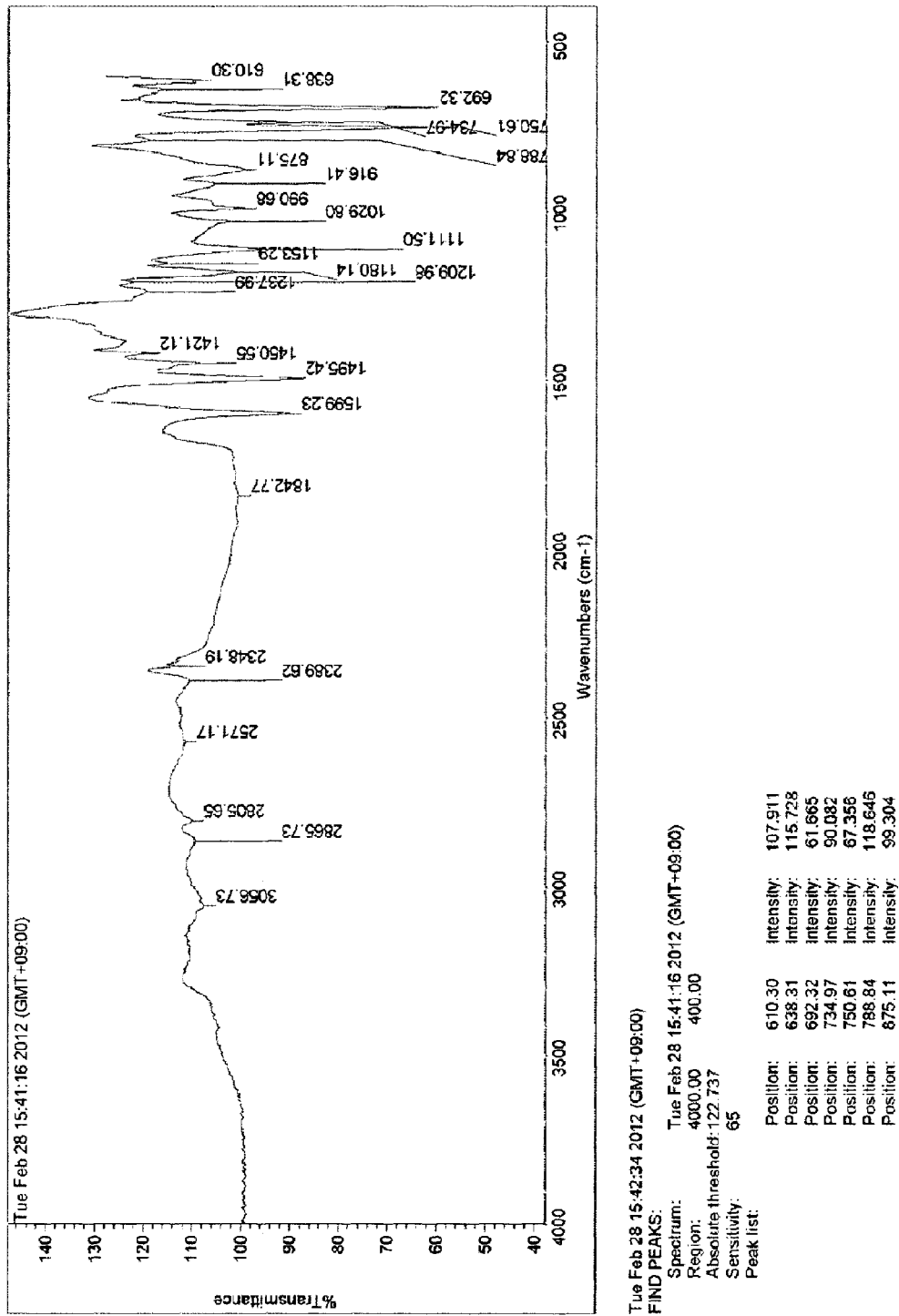
FIG. 14 shows an IR spectrum for a $H(CH_3)(C_6H_5)N^+NHCO_2^-$ compound.
Figure 15:
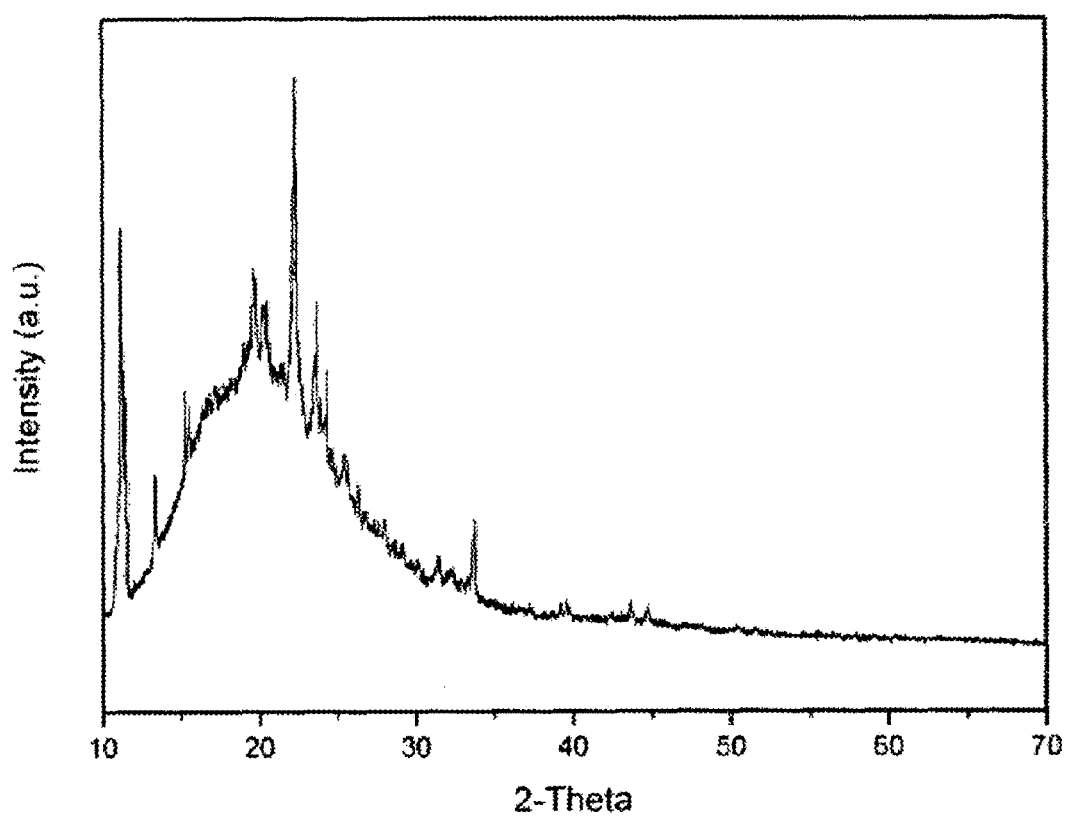
FIG. 15 shows XRD data for a $H(CH_3)(C_6H_5)N^+NHCO_2^-$ compound.

FIG. 14 and FIG. 15 show an IR spectrum and XRD data for the compound, respectively.

Example 9

The same method as that of Example 1 was used, except for using 1.21 g 1,1-dimethyl hydrazine, instead of hydrazine hydrate.

As a result of analysis, in terms of a structural formula, the powder was a compound represented by 2,2-dimethyl hydrazinium carboxylate [(CH$_3$)$_2$HN$^+$NHCO$_2$$^-$]. A yield rate of (CH$_3$)$_2$HN$^+$NHCO$_2$$^-$ obtained based on used 1,1-dimethyl hydrazine was 94% (1.96 g) or more.

Results of elemental analysis (unit %) for the product (CH$_3$)$_2$HN$^+$NHCO$_2$$^-$ Elements (calculation values, experimental values): C (34.61, 34.56), H (7.75, 7.78), N (26.91, 26.79).

$^1$H NMR (400 MHz, CD$_3$OD, 27° C.) δ 2.47 (s, 6H, CH$_3$), 4.92 (br. s, 2H, —NH & —N+H); $^{13}$C NMR (100 MHz, CD$_3$OD, 27° C.) δ 49.0 (br, CH$_3$), 160.1 (C═O).

Figure 16:
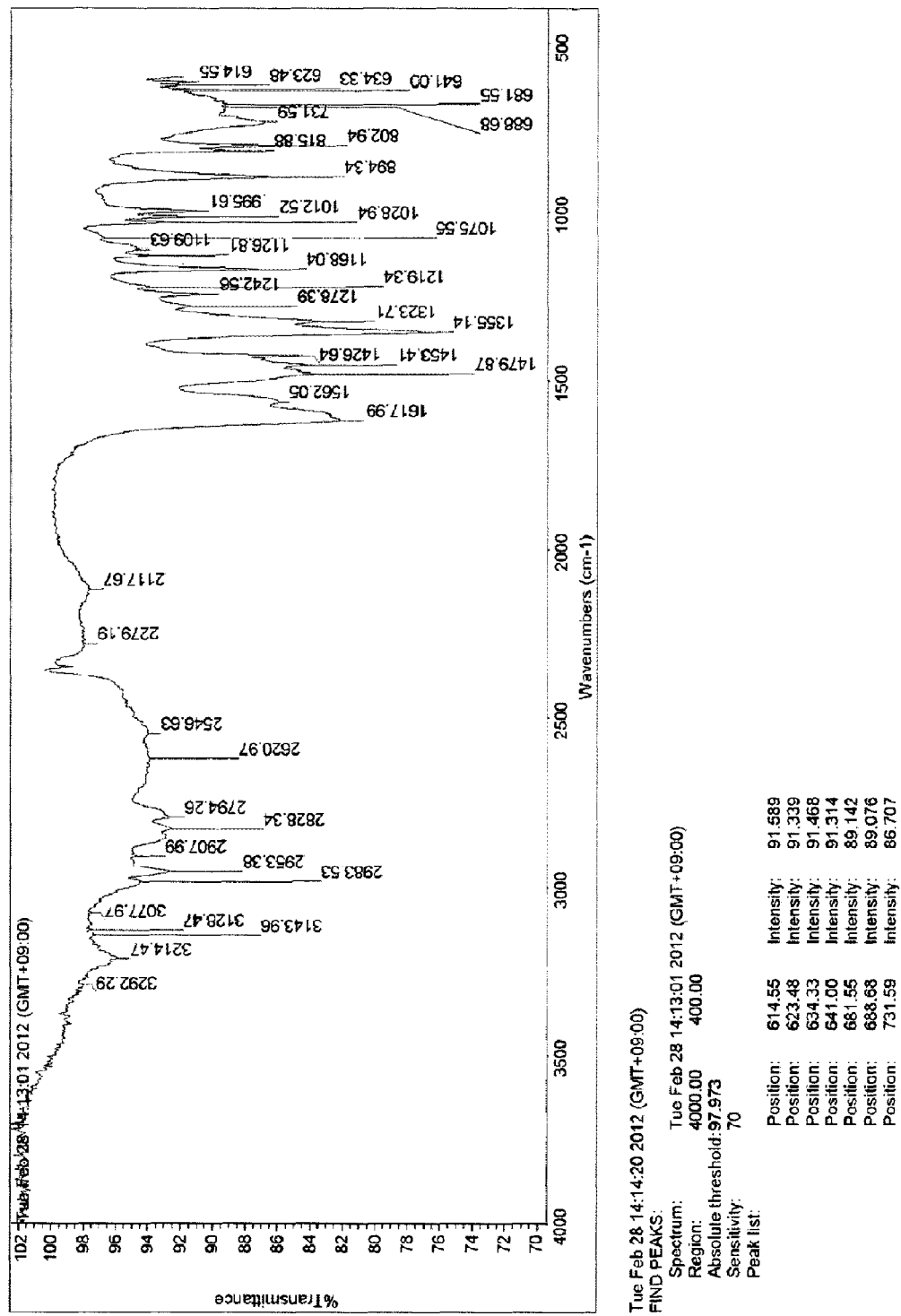
FIG. 16 shows an IR spectrum for a $(CH_3)_2HN^+NHCO_2^-$ compound.
Figure 17:
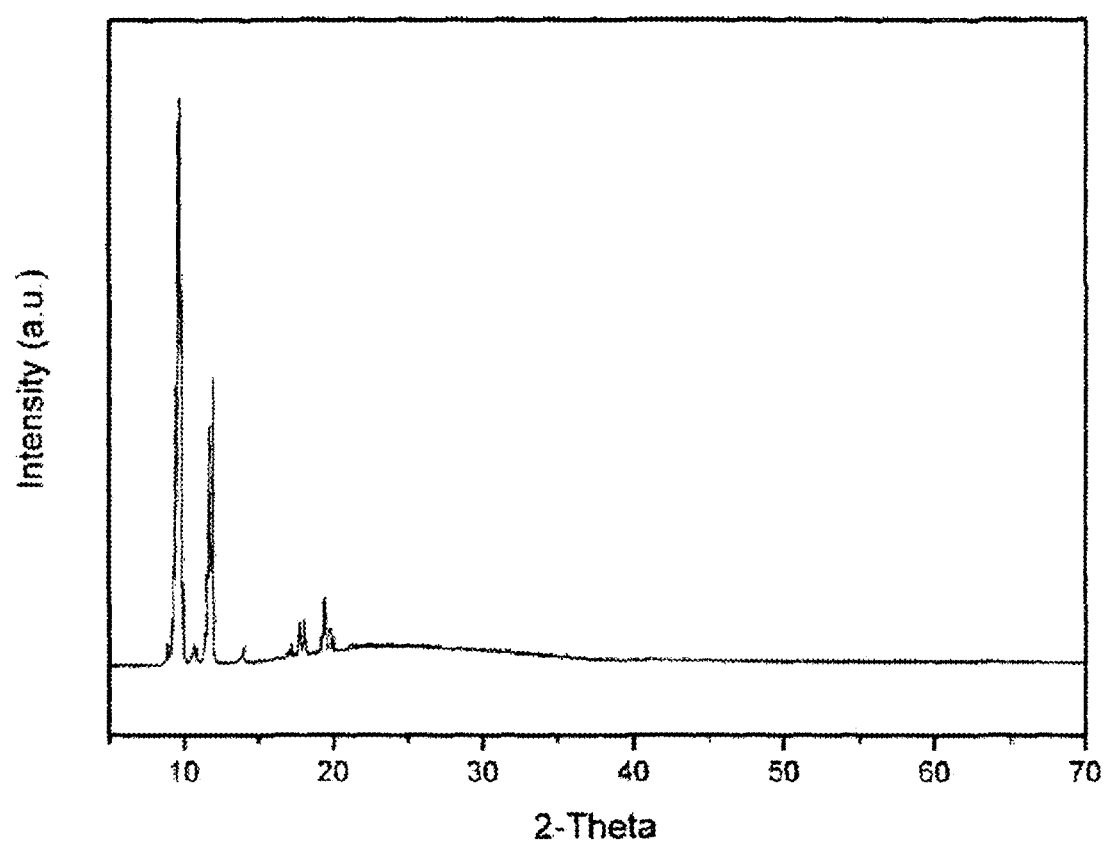
FIG. 17 shows XRD data for a $(CH_3)_2HN^+NHCO_2^-$ compound.

FIG. 16 and FIG. 17 show an IR spectrum and XRD data for the compound, respectively.

Figure 18A:
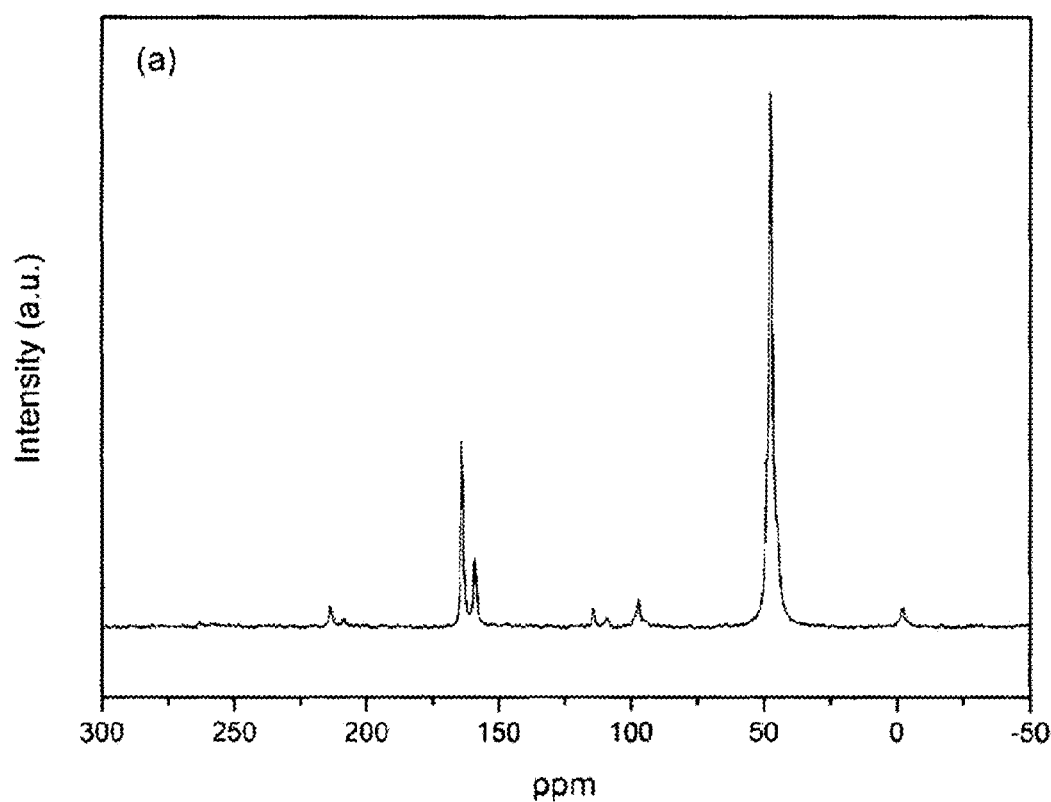
FIG. 18a and FIG. 18b show a solid-state $^{13}$C-NMR spectrum, in which $(CH_3)_2HN^+NHCO_2^-$ is being changed into dimethylammonium 2,2-dimethylhydrazinecarboxylate via Structural Formula III, and a $^{13}$C-NMR value of solid $(CH_3)_2HN^+NHCO_2^-$ changed into Structural Formula II.
Figure 18B:
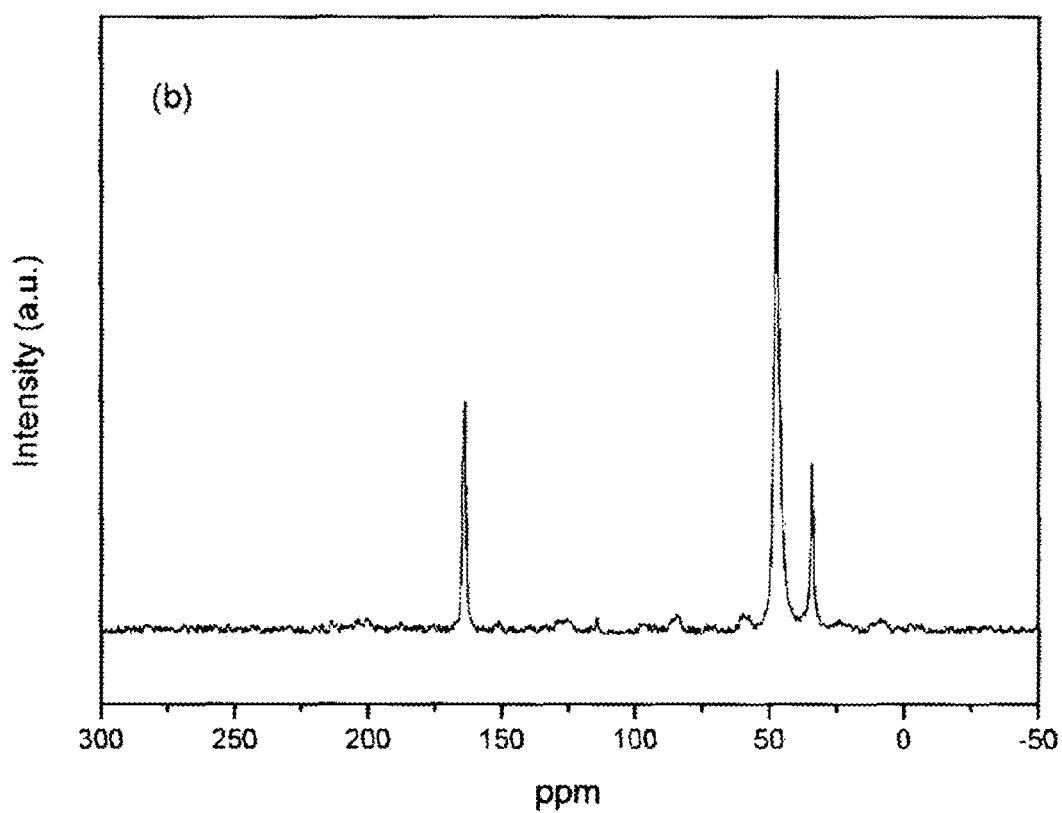
Figure 19:
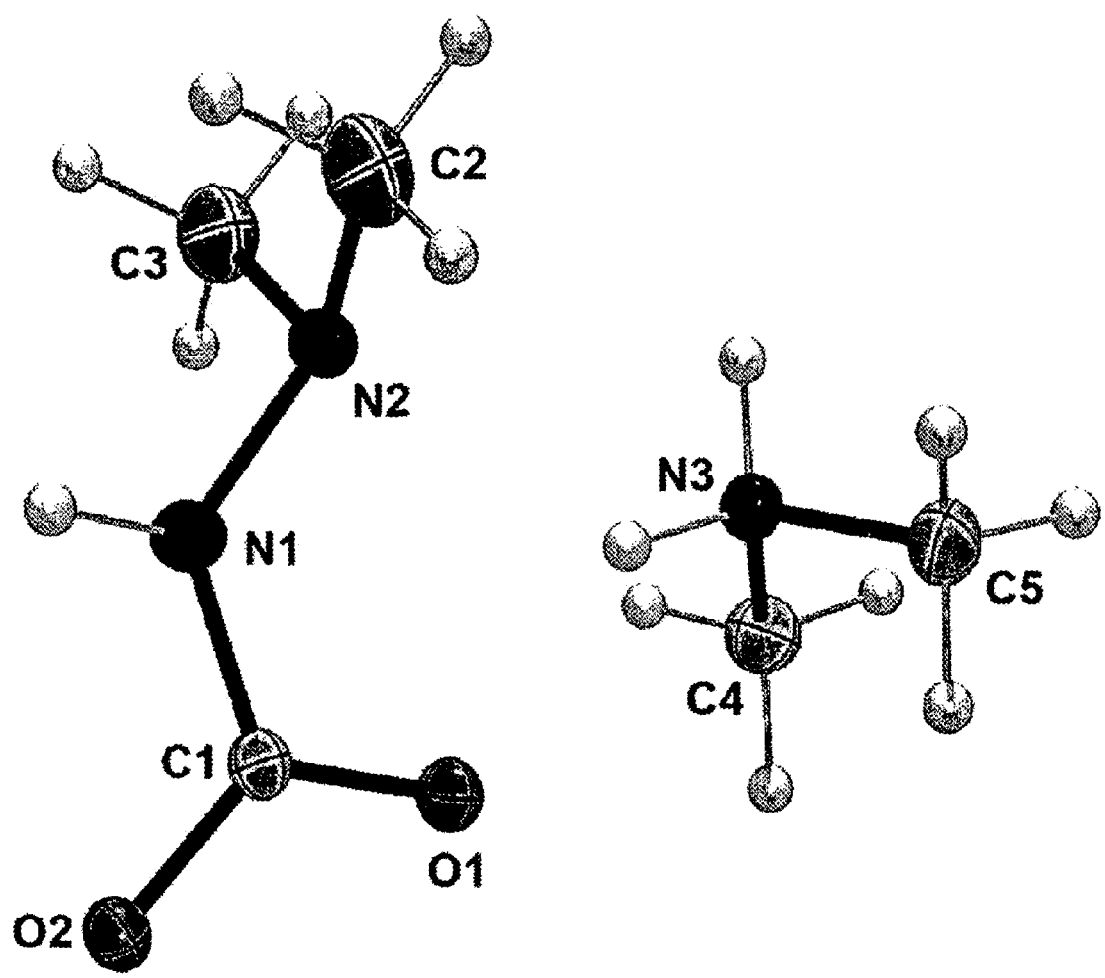
FIG. 19 shows a X-ray crystal structure (ORTEP) of dimethylammonium 2,2-dimethylhydrazinecarboxylate.

Meanwhile, this compound is changed into Structure Formula IV, i.e., dimethylammonium 2,2-dimethylhydrazinecarboxylate via the form of Structure Formula III in about three (3) months or longer at 4° C. or higher or in about seven (7) days at a room temperature, and this change was identified in the solid state by $^{13}$C NMR as shown in FIG. 18a and FIG. 18b. The compound converted into Structure Formula IV, i.e., dimethylammonium 2,2-dimethylhydrazine-carboxylate is highly stable, and thus, can be grown to be a crystal. FIG. 19 shows ORTEP of the compound prepared in the present Example.

In the compounds of Structure Formula II synthesized through the reaction of hydrazine and carbon dioxide, the hydrazine and the carbon dioxide exist at a ratio of 1:1, and when the compounds encounter a carbonyl compound, the carbon dioxide is removed even in a solvent-free condition, and the —NH$_2$ group of the hydrazine reacts with the carbonyl group so that one molecule of water is produced, and an imine compound (azine when imine is connected) is produced. Meanwhile, in the compounds of Structure Formula III, the hydrazine and the carbon dioxide exist at a ratio of 2:1, and when the compounds encounter two (2) molecules of a carbonyl compound, the carbon dioxide is removed, two (2) equivalent weights of the —NH$_2$ group reacts with the carbonyl group so that two (2) molecules of water is produced, and an imine compound is synthesized. Accordingly, Structure Formulas II and III can also be identified through the reaction with the carbonyl compound.

The Examples described below are experiments that were conducted to indirectly identify the structure suggested by the reaction to more clearly identify the structure of the compounds of Structure Formula II from which a crystal cannot be obtained.

Example 10

Figure 20:
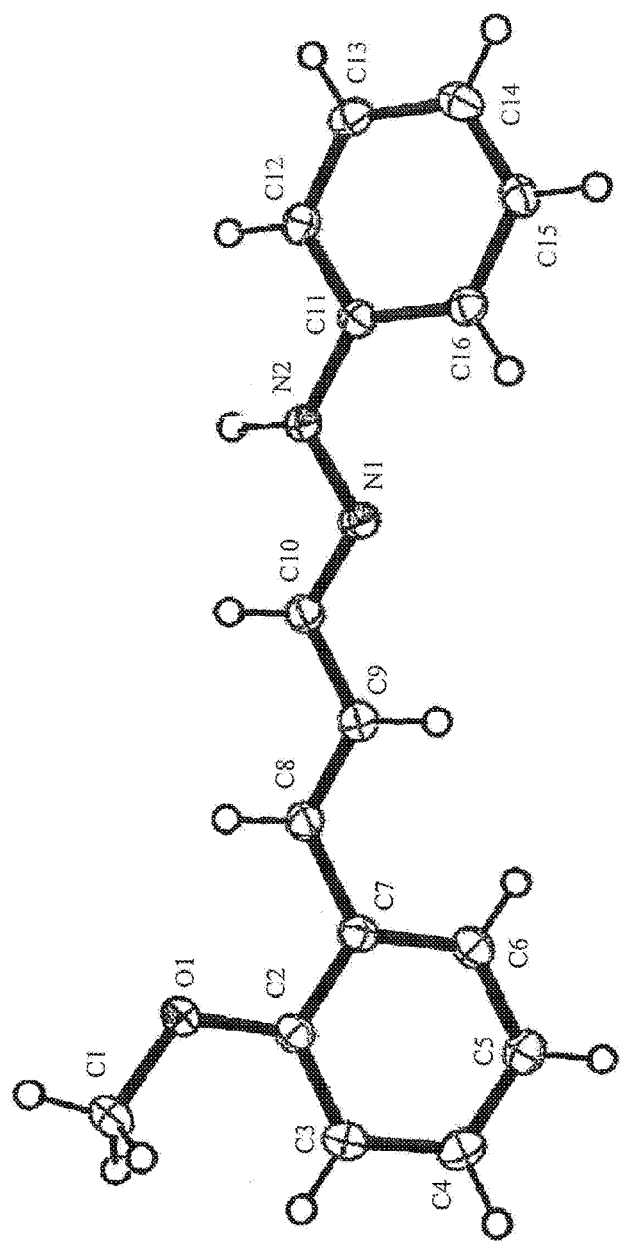
FIG. 20 shows a X-ray crystal structure (ORTEP) of an (E)-1-((E)-3-(2-methoxyphenyl)allylidene)-2-phenyl-hydrazine compound.

After a 1.52 g (10.0 mmol) compound represented by 2-phenyl hydrazinium carboxylate [H$_2$(C$_6$H$_5$)N$^+$NHCO$_2$$^-$] in a solid-state powder form was put into a mortar without a solvent together with 1.62 g (10.0 mmol) 2-methoxycynnamaldehyde to be ground and mixed with each other, they reacted with each other. Results of analysis of the product obtained after the reaction are provided below, and FIG. 20 shows ORTEP obtained from analyzing a crystal made in a CHCl$_3$/ether solvent through X-ray crystallography. From the results, it was identified that the reaction product was quantitatively produced, and that the predicted structure of Structure Formula II was correct, through inspection of the structure of the crystal.

E)-1-((E)-3-(2-methoxyphenyl)allylidene)-2-phenyl-hydrazine

Yield (2.47 g, 98%

Elemental analysis (Found: C, 76.06; H, 6.44; N, 11.27. Calc. For C$_{16}$H$_{16}$N$_2$O: C, 76.16; H, 6.39; N, 11.10%).

$^1$H NMR δ (400 MHz; CDCl$_3$; Me$_4$Si) 3.86 (3H, s, OCH$_3$), 6.87 (m, 1H, C═C—H—C), 6.94 (t, J=7.2 Hz, 1H, C—H═C—C), 7.30 (m, 3H, phenyl), 7.25 (m, 3H, phenyl), 7.51 (m, 3H, phenyl & CH═N); $^{13}$C NMR δ (100 MHz; CDCl$_3$; Me$_4$Si) 55.5 (OCH$_3$), 111.0 (CH—C═N), 112.7, 120.0, 120.8, 125.7, 126.7, 129.1, 129.2, 129.3, 141.0, 144.4 (CH, phenyl & C=C), 156.8 (C=N).

Example 11

A 1.04 g (10.0 mmol) compound represented by 2,2-dimethyl hydrazinium carboxylate [$(CH_3)_2HN^+NHCO_2^-$] was used, 4-hydroxybenzaldehyde 1.22 g (10.0 mmol) was used for a reacting carbonyl compound, and the other conditions were the same as those of Example 10. Below are results of analysis of the product obtained after the reaction.

E)-4-((2,2-dimethylhydrazono)methyl)phenol

Yield (1.59 g, 97%
Elemental analysis (Found: C, 65.57; H, 7.24; N, 17.26. Calc. For $C_3H_{12}N_2O$: C, 65.83; H, 7.37; N, 17.06%).
$^1$H NMR δ (400 MHz; CDCl$_3$; Me$_4$Si) 2.84 (6H, s, CH$_3$), 4.95 (br. s, 1H, OH), 6.72 (d, J=8.8 Hz, 2H, phenyl), 7.20 (d, J=11.68 Hz, 1H, phenyl), 7.38 (m, J=8.8 Hz, 3H, phenyl & CH=N); $^{13}$C NMR δ (100 MHz; CDCl$_3$; Me$_4$Si) 43.1 (N(CH$_3$)$_2$), 115.5, 127.3, 129.5, 134.4 (CH, phenyl), 155.6 (C=N).

From the results, it was identified that the reaction product was quantitatively produced, and that since the product was synthesized from Structure Formula II, the predicted structure is correct.

Example 12

Instead of 2,2-dimethyl hydrazinium carboxylate [$(CH_3)_2HN^+NHCO_2^-$], a 1.50 g (10.0 mmol) compound represented by dimethylammonium 2,2-dimethylhydrazine carboxylate was used, and the other conditions were the same as those of Example 11. The reaction product was exactly the same as that of Example 11, and the yield rate was almost similar to that of Example 11. Carbon dioxide and dimethylamine were removed in the gas state during the reaction.

From the results, it was identified that the reaction product was quantitatively produced, and the compound of Structure Formula IV also was in the solid state and exhibited reactivity almost similar to that of dimethyl hydrazine.

Comparative Example 1

Using Carbon Dioxide at an Atmospheric Pressure

While the same method as that of Example 1 was used, the condition of a pressure and a temperature was adjusted, and a round flask was used, instead of the high-pressure reactor. 3 mL of a hydrazine hydrate solution having 64 wt % of a ratio of contents of hydrazine was put into a cold round flask contained in an ice container, and carbon dioxide of an atmospheric pressure (about 0.1 MPa) was blown into the solution. A gel was gradually formed in the transparent solution as about 8 hours lapsed, and when carbon dioxide was further blown into the solution for 10 hours or longer, white sticky gel and solid were produced. The solid containing the gel was washed with methanol ten (10) times by using the same method as that of Example 1, and the solid in the gel form was dried in vacuum. Even after the drying, a slightly sticky material was obtained.

A yield rate obtained based on used hydrazine hydrate is about 85%. Since the result of elemental analysis does not conform with the composition of the product of Example 1, and the ratio of the elements is irregular, it is presumed that the product contains water in its solid, and materials such as $NH_2NH_3.CO_2.NH_2NH_3$ other than carbazic acid ($HCO_2N_2H_3$) are mixed therein.

Results of Elemental Analysis (Unit %) for the Product $HCO_2N_2H_3$

Elements (calculation values, experimental values): C (15.79, 13.83), H (5.30, 6.56), N (36.84, 39.72).

Mass analysis MS (EI+) m/z=32 [M]+, 31, 29, 17, 15

The following Table 1 describes the hydrazine derivative reactants reacted with carbon dioxide[a], yield rates and melting points.

TABLE 1

| entry | Reactant | mp (° C.) | bp (° C.) | product | pgase[b] | yield (%)[c] | mp (° C.) | remark[d] |
|---|---|---|---|---|---|---|---|---|
| Example 1 | $H_2N—NH_2$ | 2 | 114 | (structure) | white solid | >97 | 100 | converted to structure III |
| Example 4 | $(CH_3)HN—NH_2$ | −52 | 87 | (structure) | white solid | >97 | ~10 | FIG. 6 coverted to structure III |
| Example 5 | $PhNH—NH_2$ | 19.5 | 243.5 | (structure) | white solid | >97 | 78 | converted to structure III |
| Example 6 | 2-hydrazino-pyridine[e] | 47 | — | (structure) | white solid | >97 | 56 | converted to structure III |

TABLE 1-continued

| entry | Reactant | mp (° C.) | bp (° C.) | product | pgase[b] | yield (%)[c] | mp (° C.) | remark[d] |
|---|---|---|---|---|---|---|---|---|
| Example 7 | $HOCH_2CH_2NH-NH_2$ | — | 160.32 mmHg | (structure) | viscous gel | >97 | — | converted to structure III |
| Example 8 | $Ph(CH_3)N-NH_2$ | — | 55/0.3 mmHg | (structure) | viscous gel | >97 | — | converted to structure III |
| Example 9 | $(CH_3)_2N-NH_2$ | −57 | 64 | (structure) | white solid | >97 | [f] | converted to structure IV |

[a]$CO_2$ gas or Dry ice
[b]At 4° C.
[c]Isolated yield based on hydrazine reactant
[d]Slowly converted to the structure III
[e]Pr-2-pyridyl
[f]No mp: slowly converted to structure IV at 4° C. via the type of structure III The above description of the illustrative embodiments is provided for the purpose of illustration, and it would be understood by those skilled in the art that various changes and modifications may be made without changing technical conception and essential features of the illustrative embodiments. Thus, it is clear that the above-described illustrative embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the illustrative embodiments. It shall be understood that all modifications and embodiments conceived from the meaning and scope of the claims and their equivalents are included in the scope of the inventive concept.

We claim:

1. An anhydrous hydrazinium carboxylate derivative represented by the following Structural Formula II, which is synthesized by reacting a compound represented by the following Structural Formula I and high-pressure carbon dioxide of 7.4 MPa or higher, and is a stable solid or gel state at a room temperature:

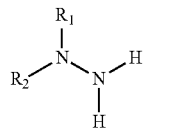

[Structural Formula I]

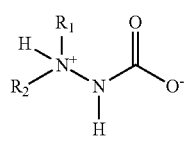

[Structural Formula II]

in Structural Formulas I and II, each of R1 and R2 is independently hydrogen; or, one of an aliphatic hydrocarbon group of 1 to 30 carbons, a substituted aliphatic hydrocarbon group of 1 to 30 carbons, a substituted aliphatic carbocyclic group of 1 to 30 carbons, a substituted aliphatic heterocyclic group of 1 to 30 carbons, a substituted aromatic cyclic group of 1 to 30 carbons, or a substituted aromatic heterocyclic group of 1 to 30 carbons; or, one of an aliphatic hydrocarbon group including at least one of Si, O, S, Se, N, P and As, an aliphatic carbocyclic group including at least one of Si, O, S, Se, N, P and As, an aliphatic heterocyclic group including at least one of Si, O, S, Se, N, P and As, or a aromatic heterocyclic group including at least one of Si, O, S, Se, N, P and As.

2. The anhydrous hydrazinium carboxylate derivative of claim 1, wherein synthesizing the compound of Structural Formula II by reacting the compound represented by Structural Formula I and carbon dioxide is conducted under a solvent-free condition.

3. The anhydrous hydrazinium carboxylate derivative of claim 1, wherein synthesizing the compound of Structural Formula II by reacting the compound represented by Structural Formula I and carbon dioxide includes Structural Formula II prepared by using one of water, an alcohol of C1 to C12, an ether of C1 to C12, or an aliphatic hydrocarbon of 1 to 30 carbons, a substituted aliphatic hydrocarbon of 1 to 30 carbons, a substituted aliphatic carbocycle of 1 to 30 carbons, a substituted aliphatic heterocyclic of 1 to 30 carbons, a substituted aromatic cycle of 1 to 30 carbons, and a substituted aromatic heterocycle of 1 to 30 carbons; or a mixed solvent thereof.

4. The anhydrous hydrazinium carboxylate derivative of claim 1, wherein the compound represented by Structural Formula I includes water.

5. The anhydrous hydrazinium carboxylate derivative of claim 4, wherein a content of the water included in the compound represented by Structural Formula I is from 1 wt % to 95 wt % with respect to a total weight of the compound and water.

6. The anhydrous hydrazinium carboxylate derivative of claim 1, wherein the compound represented by Structural Formula I does not include water.

7. The anhydrous hydrazinium carboxylate derivative of claim 1, wherein the carbon dioxide is in a gas or solid (dry ice) state.

8. An anhydrous hydrazinium carboxylate derivative represented by the following Structural Formula III, which is synthesized by reacting a compound represented by the following Structural Formula I and high-pressure carbon dioxide of 7.4 MPa or higher, and is a stable solid or gel state at a room temperature:

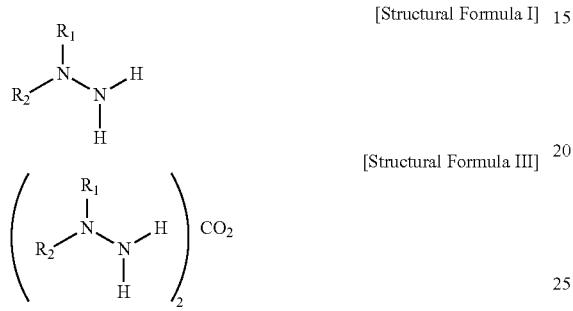

[Structural Formula I]

[Structural Formula III]

in Structural Formulas I and III, each of $R_1$ and $R_2$ is independently hydrogen; or, one of an aliphatic hydrocarbon group of 1 to 30 carbons, a substituted aliphatic hydrocarbon group of 1 to 30 carbons, a substituted aliphatic carbocyclic group of 1 to 30 carbons, a substituted aliphatic heterocyclic group of 1 to 30 carbons, a substituted aromatic cyclic group of 1 to 30 carbons, or a substituted aromatic heterocyclic group of 1 to 30 carbons; or, one of an aliphatic hydrocarbon group including at least one of Si, O, S, Se, N, P and As, an aliphatic carbocyclic group including at least one of Si, O, S, Se, N, P and As, an aliphatic heterocyclic group including at least one of Si, O, S, Se, N, P and As, or a aromatic heterocyclic group including at least one of Si, O, S, Se, N, P and As.

9. The anhydrous hydrazinium carboxylate derivative of claim 8, wherein synthesizing the compound of Structural Formula III by reacting the compound represented by Structural Formula I and carbon dioxide is conducted under a solvent-free condition.

10. The anhydrous hydrazinium carboxylate derivative of claim 8, wherein synthesizing the compound of Structural Formula III by reacting the compound represented by Structural Formula I and carbon dioxide includes Structural Formula II prepared by using one of water, an alcohol of C1 to C12, an ether of C1 to C12, or an aliphatic hydrocarbon of 1 to 30 carbons, a substituted aliphatic hydrocarbon of 1 to 30 carbons, a substituted aliphatic carbocycle of 1 to 30 carbons, a substituted aliphatic heterocycle of 1 to 30 carbons, a substituted aromatic cycle of 1 to 30 carbons, and a substituted aromatic heterocycle of 1 to 30 carbons; or a mixed solvent thereof.

11. The anhydrous hydrazinium carboxylate derivative of claim 8, wherein the compound represented by Structural Formula I includes water.

12. The anhydrous hydrazinium carboxylate derivative of claim 11, wherein a content of the water included in the compound represented by Structural Formula I is from 1 wt % to 95 wt % with respect to a total weight of the compound and water.

13. The anhydrous hydrazinium carboxylate derivative of claim 8, wherein the compound represented by Structural Formula I does not include water.

14. The anhydrous hydrazinium carboxylate derivative of claim 8, wherein the carbon dioxide is in a gas or solid (dry ice) state.

15. An anhydrous hydrazinium carboxylate detivative represented by the following Structural Formula IV, which is synthesized by reacting a compound represented by the following Structural Formula I and high-pressure carbon dioxide of 7.4 MPa or higher, and is a stable solid or gel state at a room temperature:

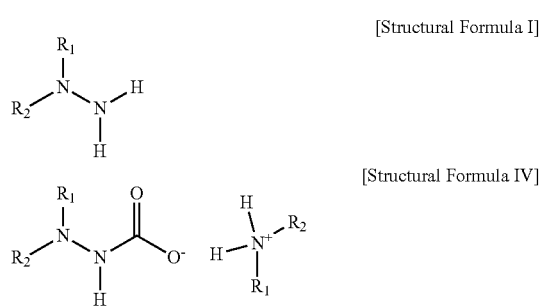

[Structural Formula I]

[Structural Formula IV]

in Structural Formulas I and IV, each of R1 and R2 is independently hydrogen; or, one of an aliphatic hydrocarbon group of 1 to 30 carbons, a substituted aliphatic hydrocarbon group of 1 to 30 carbons, a substituted aliphatic carbocyclic group of 1 to 30 carbons, a substituted aliphatic heterocyclic group of 1 to 30 carbons, a substituted aromatic cyclic group of 1 to 30 carbons, or a substituted aromatic heterocyclic group of 1 to 30 carbons; or, one of an aliphatic hydrocarbon group including at least one of Si, O, S, Se, N, P and As, an aliphatic carbocyclic group including at least one of Si, O, S, Se, N, P and As, an aliphatic heterocyclic group including at least one of Si, O, S, Se, N, P and As, or a aromatic heterocyclic group including at least one of Si, O, S, Se, N, P and As.

16. The anhydrous hydrazinium carboxylate derivative of claim 15, wherein synthesizing the compound of Structural Formula IV by reacting the compound represented by Structural Formula I and carbon dioxide is conducted under a solvent-free condition.

17. The anhydrous hydrazinium carboxylate derivative of claim 15, wherein synthesizing the compound of Structural Formula IV by reacting the compound represented by Structural Formula I and carbon dioxide includes Structural Formula II prepared by using one of water, an alcohol of C1 to C12, an ether of C1 to C12, or an aliphatic hydrocarbon of 1 to 30 carbons, a substituted aliphatic hydrocarbon of 1 to 30 carbons, a substituted aliphatic carbocycle of 1 to 30 carbons, a substituted aliphatic heterocycle of 1 to 30 carbons, a substituted aromatic cycle of 1 to 30 carbons, and a substituted aromatic heterocycle of 1 to 30 carbons; or a mixed solvent thereof.

18. The anhydrous hydrazinium carboxylate derivative of claim 15, wherein the compound represented by Structural Formula I includes water.

19. The anhydrous hydrazinium carboxylate derivative of claim 15, wherein a content of the water included in the compound represented by Structural Formula I is from1 wt % to 95 wt % with respect to a total weight of the compound and water.

20. The anhydrous hydrazinium carboxylate derivative of claim 15, wherein the compound represented by Structural Formula I does not include water.

* * * * *